US012662434B2

(12) United States Patent
Peterson et al.

(10) Patent No.: US 12,662,434 B2
(45) Date of Patent: Jun. 23, 2026

(54) DIRECT CONVERSION OF METHANE TO $C_2$ AND HIGHER HYDROCARBONS

(71) Applicants: Brown University, Providence, RI (US); SK Innovation Co., Ltd., Seoul (KR)

(72) Inventors: Andrew Peterson, Providence, RI (US); Franklin Goldsmith, Providence, RI (US); Jongyoon Bae, Providence, RI (US); Dongmin Yun, Daejeon (KR); Juhwan Im, Daejeon (KR); Dokyoung Kim, Daejeon (KR)

(73) Assignees: Brown University, Providence, RI (US); SK Innovation Co., Ltd., Seoul (KR)

( * ) Notice: Subject to any disclaimer, the term of this patent is extended or adjusted under 35 U.S.C. 154(b) by 123 days.

(21) Appl. No.: 18/281,837

(22) PCT Filed: Mar. 21, 2022

(86) PCT No.: PCT/US2022/021081
§ 371 (c)(1),
(2) Date: Sep. 13, 2023

(87) PCT Pub. No.: WO2022/203985
PCT Pub. Date: Sep. 29, 2022

(65) Prior Publication Data
US 2024/0158316 A1 May 16, 2024

Related U.S. Application Data

(60) Provisional application No. 63/165,233, filed on Mar. 24, 2021.

(51) Int. Cl.
*C07C 2/76* (2006.01)

(52) U.S. Cl.
CPC .................................... *C07C 2/76* (2013.01)

(58) Field of Classification Search
CPC . C07C 2/76; C07C 2521/08; C07C 2523/745; C07C 9/06; C07C 11/04;
(Continued)

(56) References Cited

U.S. PATENT DOCUMENTS 4,973,777 A 11/1990 Alagy et al.
7,977,519 B2 * 7/2011 Iaccino .................... C07C 2/78
585/407

(Continued)

OTHER PUBLICATIONS

Jun. 8, 2022—(WO) International Search Report & Written Opinion—App. No. PCT/US2022/021081.

(Continued)

*Primary Examiner* — Ali Z Fadhel
(74) *Attorney, Agent, or Firm* — Banner & Witcoff, Ltd.

(57) ABSTRACT

Aspects of the invention are associated with the discovery of processes for converting methane ($CH_4$), present in a methane-containing feed that may be obtained from a variety of sources such as natural gas, to higher hydrocarbons (e.g., $C_2^+$ hydrocarbons) such as $C_2$ hydrocarbons (e.g., ethane, ethylene, and acetylene) and aromatic hydrocarbons (e.g., benzene, one or more $C_1$- or $C_2$-substituted benzenes, and/or one or more fused ring aromatic hydrocarbons). Representative processes involve direct, non-oxidative methane conversion (NOMC), such that the need for an oxidant to form CO as an intermediate may advantageously be avoided. This reduces overall complexity and the tendency to promote unwanted side reactions that reduce hydrocarbon yields and lead to $CO_2$ production.

18 Claims, 13 Drawing Sheets

(58) Field of Classification Search
CPC ......... C07C 11/24; C07C 15/02; C07C 15/20; C10G 50/00
See application file for complete search history.

(56) References Cited

U.S. PATENT DOCUMENTS

2008/0058564 A1 3/2008 Iaccino et al.
2018/0169621 A1* 6/2018 Bao .......................... B01J 23/30
2020/0354287 A1* 11/2020 Iyer ........................... C07C 2/82
2020/0392416 A1* 12/2020 Marker .................. C10G 47/32

OTHER PUBLICATIONS

Kim et al., “Mechanistic and microkinetic study of non-oxidative methane coupling on a single-atom iron catalyst,” Communications Chemistry, vol. 3, No. 58, pp. 1-8 (May 8, 2020).

* cited by examiner

DIRECT CONVERSION OF METHANE TO $C_2$ AND HIGHER HYDROCARBONS

RELATED APPLICATION DATA

This application is a National Stage Application under 35 U.S.C. 371 of co-pending PCT application PCT/US2022/021081 designating the United States and filed Mar. 21, 2022; which claims priority to U.S. Provisional Application No. 63/165,233 filed on Mar. 24, 2021, each of which are hereby incorporated by reference in their entireties.

FIELD OF THE INVENTION

Aspects of the invention relate to processes and systems for the conversion of methane to produce higher hydrocarbons, and more particularly $C_2^+$ hydrocarbons such as ethane, ethylene, and acetylene, as well as aromatic hydrocarbons (e.g., benzene and other single ring aromatics) having commercially relevant uses.

DESCRIPTION OF RELATED ART

The ongoing search for alternatives to crude oil, as a source of carbon for the production of hydrocarbon fuels and specialty chemicals, particularly petrochemical precursors such as light olefins and aromatics, is increasingly driven by a number of factors. These include diminishing petroleum reserves, higher anticipated energy demands, and heightened concerns over greenhouse gas (GHG) emissions from sources of non-renewable carbon. In view of its abundance in natural gas reserves and oil-associated gases, methane has become the focus of a number of possible synthesis routes. Currently, natural gas is the most underutilized of fossil resources, and it is frequently flared (combusted) in large quantities, particularly in the case of "stranded" natural gas or other sources that are too isolated and/or lacking in quantity, rendering their transport to large-scale processing facilities an uneconomical proposition. In addition, fracking technology has resulted in decreasing prices of natural gas prices in the U.S., with an increasing supply of this resource globally. Moreover, methane is one of the most common products that can be produced from renewable resources, such as via anaerobic bacterial digestion of biowastes, supercritical water gasification of biomass, the collection of gases from landfills, or the electrochemical reduction of carbon dioxide. Therefore, the efficient conversion of methane to longer-chained hydrocarbons has the potential to generate significant value, if practiced on the industrial scale. It is not an overstatement to refer to the utilization and upgrading of methane carbon in this manner as the "holy grail" of fossil energy conversion.

Relevant to the thermodynamic considerations involved in the conversion of methane, the tetrahedral and symmetrical configuration of the carbon and hydrogen atoms forming this molecule gives rise to its high stability, which hinders its direct conversion to higher hydrocarbons (e.g., aromatic hydrocarbons) that are recognized in the marketplace as valuable components of liquid fuels and/or building blocks for petrochemicals (e.g., polyethylene). Widely practiced commercial processes for producing liquid fuels from natural gas therefore rely on so-called indirect conversion or "oxidative coupling" routes, whereby methane is first oxidized to form synthesis gas (or "syngas"), i.e., a mixture of CO and $H_2$. This intermediate has sufficient reactivity for further conversion to higher value products including liquid fuels. The oxidant that reacts with methane in this initial step may be (i) $H_2O$, in the case of steam reforming, (ii) $CO_2$, in the case of dry reforming, or (iii) one or both of these oxidants, in combination with $O_2$, in the case of autothermal reforming. In the last case, the introduction of molecular oxygen results in "partial oxidation" of methane, thereby offsetting the heat input required to sustain the endothermic steam reforming and dry reforming reactions. Following any of these modes of oxidative coupling, using reforming and/or partial oxidation, the resultant syngas-containing effluent is then typically subjected to Fisher-Tropsch (FT) synthesis to produce hydrocarbons and/or alcohols of varying molecular weights, depending on the particular operating conditions and catalyst used. For example, in a methanol-to-gasoline (MTG) conversion complex, methanol is the targeted product of FT synthesis, which is an intermediate for subsequent dehydration to the desired liquid hydrocarbons. Whether such liquid fuels are obtained directly from FT synthesis or through an alcohol intermediate, the use of methane reforming as an initial processing step has provided the economic justification for transporting natural gas over long distances.

Nonetheless, such indirect conversion pathways from methane to higher hydrocarbons require considerable complexity, arising from gas pretreatment (e.g., $H_2S$ removal), in addition to multiple conversion steps. This combination of reforming and FT synthesis therefore involves high capital expenditures and substantial operating capacity to achieve the needed economies of scale. Moreover, these known methods suffer from poor selectively to gasoline boiling-range hydrocarbons and result in substantial carbon dioxide emissions. In particular, with respect to the oxidative coupling reaction environment, the increased reactivity of higher, $C_2^+$ hydrocarbons over methane leads to their undesired, sequential oxidation to thermodynamically favored COx (CO or $CO_2$). This increases production costs, in terms of both the loss of desired, higher hydrocarbons, as well as the associated, detrimental environmental impact.

Direct routes to higher hydrocarbons that have been studied extensively, and particularly the oxidation of methane with $O_2$ to produce alkanes and $H_2O$, have been met with a number of significant challenges. These include thermodyamically favorable reaction pathways that lead to further oxidation ("over oxidation") of the desired hydrocarbons and oxygenates, resulting in substantial $CO_2$ formation. In addition, management of the highly exothermic oxidation reaction poses a number of practical problems in terms of process design. The catalytic oxidation of methane and other hydrocarbons to form higher hydrocarbons is described, for example in U.S. Pat. No. 5,043,505. In addition, the use of $S_2$ or $H_2S$, rather than $O_2$ has been investigated for the "soft oxidation" of methane as a route to hydrocarbon production, in which the product selectivity and process thermodynamics are more easily controlled, due to lower free energy losses and over oxidation potential. These routes, however, generally proceed through intermediate carbon disulfide, $CS_2$, production and involve the handling of potentially hazardous gases.

Other processes for the conversion of methane to higher value products including $C_2$ hydrocarbons (e.g., acetylene, ethylene, ethane) and higher hydrocarbons (e.g., aromatic hydrocarbons such as benzene and naphthalene), which in combination may be referred to as $C_2^+$ hydrocarbons, are therefore of interest in the art.

SUMMARY OF THE INVENTION

Aspects of the invention are associated with the discovery of processes for direct, non-oxidative methane conversion (NOMC) to $C_2^+$ hydrocarbons, which are generally higher value products relative to methane and which can be recovered for use as fuel components, specialty chemicals, or intermediates for further processing such as in the manufacture of petrochemicals including plastics (e.g., polyolefins, polyamides, polyaromatics such as polyesters and polystyrene, etc.). Representative $C_2^+$ hydrocarbons include the $C_2$ hydrocarbons ethane, ethylene, and acetylene, as well as single ring aromatic hydrocarbons, such as benzene, toluene, ethylbenzene, styrene, and ethynylbenzene; fused, 2-ring aromatic hydrocarbons (i.e., having at least one aromatic ring), such as naphthalene and indene; and fused, 3-ring hydrocarbons (i.e., having at least one aromatic ring), such as acenaphthylene and acenaphthene. Further examples of $C_2^+$ hydrocarbons, and classes of these hydrocarbons, according to various embodiments, are described below.

Embodiments of the invention are directed to processes for converting methane in a methane-containing feed (e.g., comprising natural gas) to $C_2^+$ hydrocarbons, which processes advantageously avoid the need for an oxidant to form CO as an intermediate, and component of syngas, for the further reaction to form the desired products. Direct NOMC to $C_2^+$ hydrocarbons, in a methane conversion reactor operating under methane conversion conditions, thereby reduces complexity and the tendency to promote unwanted side reactions that reduce hydrocarbon yields and lead to $CO_2$ production. According to particular embodiments, therefore, oxidants ($H_2O$, $CO_2$, $O_2$) or "soft" oxidants ($H_2S$, S) may be substantially absent from the methane-containing feed. For example any one of $H_2O$, $CO_2$, $O_2$, $H_2S$, and S, or any combination of two or more of these, may be present in the methane-containing feed in concentration of less than about 5 vol-%, less than about 1 vol-%, or less than about 1000 vol-ppm. In other embodiments, in the case of one of more of such oxidants or "soft" oxidants being present in the methane-containing feed (e.g., as minor components of natural gas), these do not undergo substantially any conversion and/or substantially any reaction with methane. For example, the conversion of any one of $H_2O$, $CO_2$, $O_2$, $H_2S$, and S, or the combined conversion of any two or more of these, in the methane conversion reactor, may be less than about 5 wt-%, less than about 1 wt-%, or less than about 0.5 wt-%.

Without being bound by theory, direct NOMC to $C_2^+$ hydrocarbons involves the conversion of methane, having a 4:1 H:C ratio, to any higher hydrocarbon (hydrocarbon having two or more carbon atoms) necessarily having a lower WC ratio, with the accompanying generation of hydrogen. Accordingly, NOMC may encompass one or more the reactions methane dehydrogenation, methane dehydrodimerization (in the case of producing $C_2$ hydrocarbons), methane dehydrooligomerization (in the case of producing $C_2^+$ non-cyclic hydrocarbons), methane dehydrocylization (in the case of producing cyclic hydrocarbons), and methane dehydroaromatization (in the case of producing aromatic hydrocarbons). In the case of the simple reactions of methane to form ethane or ethylene, for example, these can proceed according to $$2CH_4 \longrightarrow C_2H_6 + H_2 \quad \text{or}$$

$$2CH_4 \longrightarrow C_2H_4 + 2H_2.$$

Because the formation of any $C_2^+$ hydrocarbon from methane in this manner can proceed through the liberation of hydrogen (e.g., according to the reactions depicted above), conventional equilibrium considerations (e.g., according to Le Chatelier's principle) would indicate that reducing hydrogen concentration should serve to drive the direct NOMC reactions forward. In this regard, aspects of the invention relate to contrary findings, including those based on microkinetic models, that increasing $H_2$ concentration in the reaction system can unexpectedly lead to a favorable shift toward production of the desired $C_2^+$ hydrocarbons. Such models further predicted other operating parameters, including reductions in operating pressure and residence time, which would likewise be beneficial in achieving the targeted, effective conversion of methane to higher hydrocarbons with minimal formation of detrimental coke. In view of experimental work confirming these findings, other aspects of the invention relate to the discovery of suitable combinations of methane conversion conditions, including one or more of temperature, pressure, hydrogen concentration, residence time, and others, optionally maintained in the presence of a suitable catalyst within the methane conversion reactor, which lead to conversions, product yields, and sufficiently low by-product (e.g., coke) yields, as needed for economic viability on a commercial scale.

Particular embodiments of the invention are directed to processes for converting a methane-containing feed to $C_2^+$ hydrocarbons. The processes comprise providing (e.g., by flowing or otherwise introducing) the methane-containing feed to a methane conversion reactor operating under methane conversion conditions, to obtain a product, such as an effluent of the methane conversion reactor, comprising the $C_2^+$ hydrocarbons. These $C_2^+$ hydrocarbons are advantageously at least partly, but preferably substantially or completely, obtained from conversion of the methane, i.e., carbon originally present in the methane is used for the formation of the $C_2^+$ hydrocarbons, although other carbon sources of part of the $C_2^+$ hydrocarbons in the product are possible (e.g., carbon from unconverted or converted $C_2^+$ hydrocarbons present in the methane-containing feed). Representative methane conversion conditions include an absolute pressure of less than about 1 megapascals (MPa) and a residence time (e.g., computed as an average or bulk residence time in the methane conversion reactor) of less than about 60 seconds.

Further embodiments are directed to these and other processes in which the product is separated (e.g., in a downstream separation step) by condensing at least a portion of the $C_2^+$ hydrocarbons in a liquid being enriched in (e.g., having a higher weight or volume percentage of) the $C_2^+$ hydrocarbons, relative to the product. The recovery of a liquid may be especially desirable in the case of producing aromatic hydrocarbons, which may be used directly as a liquid fuel or fuel blending component (e.g., gasoline or a gasoline blending component) or processed further, for example in the manufacture of specialty chemicals or petrochemicals including plastics. According to specific embodiments, the processes comprise providing (e.g., by flowing or otherwise introducing) the methane-containing feed to a methane conversion reactor operating under methane conversion conditions, to obtain a product, such as an effluent of the methane conversion reactor, comprising (i) the $C_2^+$ hydrocarbons (at least partly obtained from conversion of the methane), including one or more $C_2$ hydrocarbons and one or more aromatic hydrocarbons, and further comprising (ii) hydrogen and unconverted methane. The processes further comprise separating the product, by condensing from this product a liquid, with this liquid being enriched in (e.g., having a higher weight or volume percentage of) the one or more aromatic hydrocarbons, relative to the product.

Yet further particular embodiments are directed to these and other processes in which the product is separated, and also in which the overall conversion and yield parameters of the process can be increased compared to "once-through" operation, by recycling hydrogen and/or unconverted methane to the methane conversion reactor. Specifically, the condensing of a liquid from the product, according to the product separation, may provide a vapor, with this vapor being enriched in (e.g., having a higher weight or volume percentage of) both the hydrogen and the unconverted methane, relative to the product. Optionally, depending on the methane conversion conditions (e.g., the extent to which they form $C_2$ hydrocarbons, if any) and conditions used in the product separation (e.g., pressure and temperature), the vapor may also be enriched in (e.g., have a higher weight or volume percentage of) the one or more $C_2$ hydrocarbons, relative to the product. Whether $C_2$ hydrocarbons, if any, are preferentially separated into a liquid fraction or a vapor fraction of the product, representative processes may comprise recycling at least a portion of the vapor to the methane conversion reactor, thereby utilizing the hydrogen and unconverted methane, an particularly the carbon content of the latter, for the further production of $C_2^+$ hydrocarbons.

Still further embodiments are directed to these and other processes in which hydrogen concentration, for example in vol-%, or hydrogen partial pressure, for example in kilopascals (kPa), may be adjusted to influence a performance parameter of the processes. Such adjustment may be made in a manner considered counterintuitive given the reaction chemistry, including the co-production of hydrogen with $C_2^+$ hydrocarbons. Particular embodiments are directed to processes for converting a methane-containing feed to $C_2^+$ hydrocarbons and hydrogen. The processes comprise providing (e.g., by flowing or otherwise introducing) the methane-containing feed to a methane conversion reactor operating under methane conversion conditions, to obtain a product, such as an effluent of the methane conversion reactor, comprising the $C_2^+$ hydrocarbons. The processes may further comprise, in response to a performance parameter of the process that is below a target value, increasing a hydrogen concentration or hydrogen partial pressure in the methane conversion reactor. For example, representative performance parameters include a conversion of methane in the methane-containing feed or a yield of the $C_2^+$ hydrocarbons. With the understanding that increasing hydrogen concentration or hydrogen partial pressure in the methane conversion reactor can drive the desired reaction forward (contrary to expectations based on the reaction chemistry alone), this adjustment may be carried out, for example, by increasing the amount, or relative amount, of hydrogen in the feed (e.g., by increasing the feed $H_2$:$CH_4$ molar ratio). Conversely, processes may otherwise, or in combination, comprise decreasing a hydrogen concentration or hydrogen partial pressure in the methane conversion reactor, in response to a performance parameter of the process that is above a target value.

Other embodiments are directed to any of the processes described herein, in which the methane conversion reactor contains a catalyst, such as a solid catalyst described herein, that catalyzes the NOMC reaction.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures.

Figure 1:
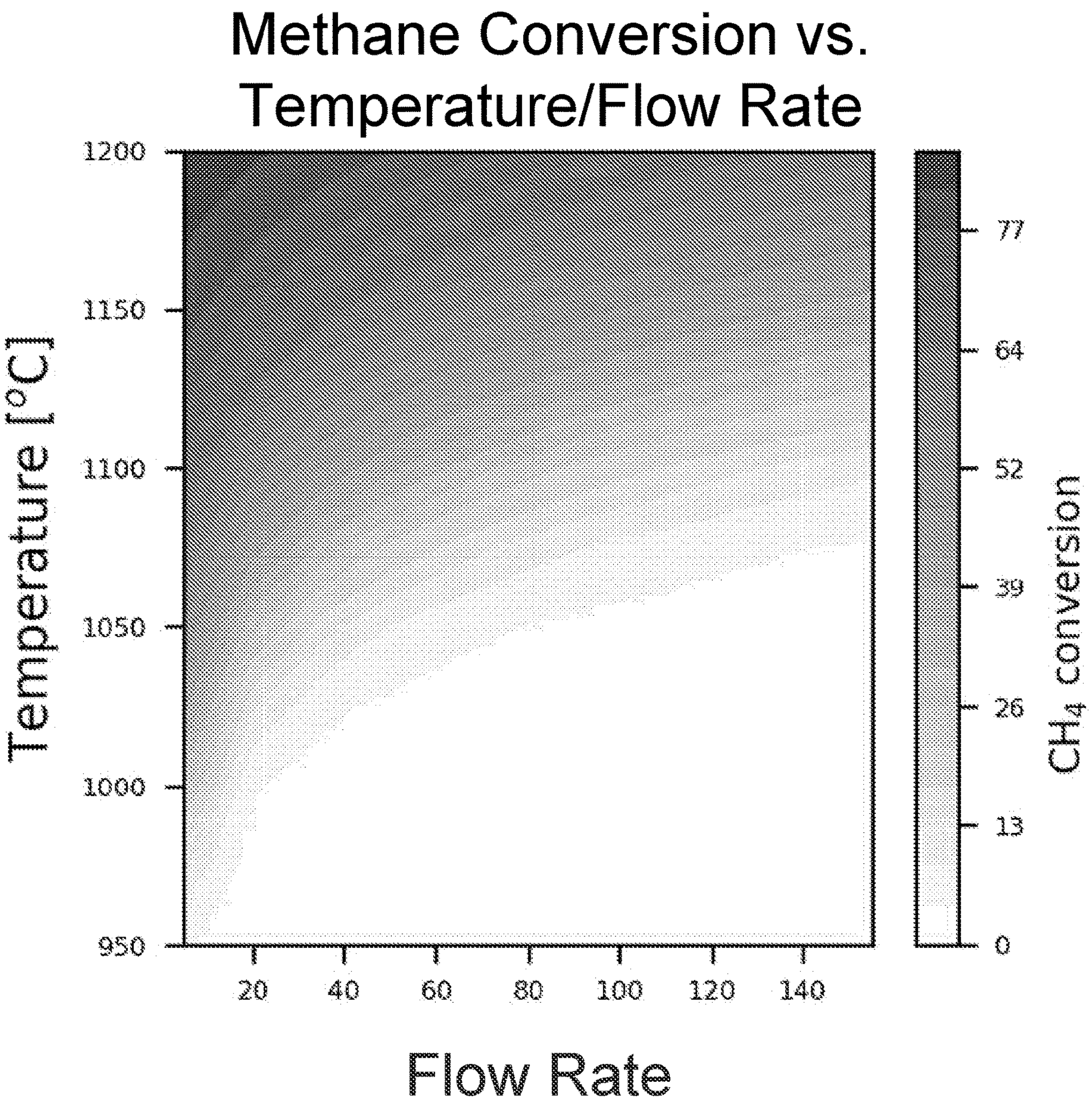
FIG. 1 depicts the conversion of methane as a function of both reaction temperature and flow rate.

The figures should be understood to illustrate the practice of specific embodiments of the invention and/or to demonstrate the relevant principles involved, in order to facilitate explanation and understanding. The values in the figures that are given for the flow rate of the methane-containing feed should be understood as relative values that will necessarily scale with the overall scale of the process. However, in specific embodiments the values given for the flow rate correspond to values in normal milliliters per minute (ml/min). As is readily apparent to one of skill in the art having knowledge of the present disclosure, other processes for converting a methane-containing feed to higher hydrocarbons, carried out under other conditions to obtain other performance objectives, are within the scope of the invention as disclosed herein.

DETAILED DESCRIPTION

The term "$C_2^+$ hydrocarbons" refers to hydrocarbons having two or more carbon atoms, with examples including $C_2$-$C_{14}$ hydrocarbons (i.e., one or more hydrocarbons having from 2 to 14 carbon atoms), $C_2$-$C_{10}$ hydrocarbons (i.e., one or more hydrocarbons having from 2 to 10 carbon atoms), $C_2$-$C_8$ hydrocarbons (i.e., one or more hydrocarbons having from 2 to 8 carbon atoms), $C_2$-$C_7$ hydrocarbons one or hydrocarbons having from 2 to 7 carbon atoms), and $C_2$-$C_6$ hydrocarbons one or more hydrocarbons having from 2 to 6 carbon atoms). Specific examples of $C_2^+$ hydrocarbons are the $C_2$ hydrocarbons ethane, ethylene, and acetylene, and other specific examples are single ring aromatic hydrocarbons; fused, 2-ring hydrocarbons having at least one aromatic ring; and fused, 3-ring hydrocarbons having at least one aromatic ring. Accordingly, the $C_2^+$ hydrocarbons, in particular embodiments, may comprise (i) the $C_2$ hydrocarbons ethane, ethylene, and acetylene; (ii) single ring aromatic hydrocarbons; (iii) fused, 2-ring hydrocarbons having at least one aromatic ring, (iv) fused, 3-ring hydrocarbons having at least one aromatic ring, or (v) any combination of (i), (ii), (iii), and/or (iv). Single ring aromatic hydrocarbons include benzene and benzene that is substituted at one or more ring positions with a methyl, ethyl, ethenyl, or ethynyl substituent, such as toluene (methylbenzene), ethylbenzene, styrene (ethenyl benzene), and ethynylbenzene; fused, 2-ring hydrocarbons having at least one aromatic ring include naphthalene, indene, and their derivatives that are partially saturated (e.g., dihydro and tetrahydro derivatives) and/or substituted at one or more ring positions with a methyl, ethyl, ethenyl, or ethynyl substituent; fused, 3-ring hydrocarbons having at least one aromatic ring include acenaphthylene, acenaphthene, and their derivatives that are partially saturated (e.g., dihydro and tetrahydro derivatives) and/or substituted at one or more ring positions with a methyl, ethyl, ethenyl, or ethynyl substituent. According to a particular embodiment, the $C_2^+$ hydrocarbons may comprise $C_2$ hydrocarbons, as described above, and one or more aromatic hydrocarbons, such as benzene, one or more $C_1$- or $C_2$-substituted benzenes, and/or one or more fused ring aromatic hydrocarbons.

Whereas the term "$C_1^+$ hydrocarbons" refers in general to hydrocarbons having two or more carbon atoms, references herein to "$C_2^+$ hydrocarbons" should be understood to also disclose more specific embodiments in which "$C_2^+$ hydrocarbons" is replaced with any of the groups of hydrocarbons (e.g., $C_2$-$C_7$ hydrocarbons) and/or any of the individual hydrocarbons or combinations of individual hydrocarbons noted above. Therefore, for example, references to values of a selectivity to, or yield of, $C_2^+$ hydrocarbons herein should be understood to also disclose (i) the same values of selectivity to, or yield of, all hydrocarbons having two or more carbon atoms; (ii) the same values of selectivity to, or yield of, ethane, ethylene, and acetylene in combination; (iii) the same values of selectivity to, or yield of, $C_2$-$C_7$ hydrocarbons in combination; and (iv) the same values of selectivity to, or yield of, ethane, benzene, and toluene, in combination, etc.

The expressions "wt-%," "mol-%," and "vol-%" are used herein to designate weight percentages, molar percentages, and volume percentages, respectively. The expressions "wt-ppm," "mol-ppm," and "vol-ppm" designate weight parts per million, molar parts per million, and volume parts per million, respectively. For ideal gases, "mol-%" and "mol-ppm" are equal to percentages by volume, i.e., vol-%, and parts per million by volume, i.e., vol-ppm, respectively.

Embodiments of the invention relate to a process for converting methane in a methane-containing feed to higher hydrocarbons (e.g., $C_2^+$ hydrocarbons). Representative methane-containing feeds are gases comprising at least about 20 vol-% (e.g., from 20 vol-% to about 99 vol-% or more) $CH_4$, with such gases typically comprising at least about 35 vol-% (e.g., from about 35 vol-% to about 95 vol-%) $CH_4$, and often comprising at least about 50 vol-% (e.g., from about 50 vol-% to about 90 vol-%) $CH_4$. Methane-containing feeds may include gaseous hydrocarbon impurities such as ethane and propane, as well as non-hydrocarbon impurities such as CO and $CO_2$. Depending on particular source(s) of its component(s), the methane-containing feed may include sulfur-containing compounds, such as $H_2S$, although in some embodiments the upstream removal of $H_2S$ (e.g., by amine scrubbing) may be desired to prolong the life of a catalyst, if used in the methane conversion reactor or possibly in a downstream conversion step. In general, the methane-containing feed may include a total content of sulfur, whether present as $H_2S$ or other sulfur-containing compounds, of less than about 1 vol-%, less than about 0.1 vol-%, or less than about 500 vol-ppm. In general, solids such as biomass may be substantially absent from the methane-containing feed, i.e., this feed may comprise less than 0.1 wt-% of solids.

According to particular embodiments, the methane-containing feed refers to the entirety of the material that is fed to the methane conversion reactor (e.g., including hydrogen according to embodiments described herein).

Important methane-containing feeds are those comprising natural gas, such as stranded natural gas, which, using known processes, cannot be economically upgraded to $C_2^+$ hydrocarbons. Other methane-containing feeds may be obtained from coal or biomass (e.g., char) gasification, from a biomass digester, or as effluents from biofuel production processes (e.g., pyrolysis processes and fatty acid/triglyceride hydroconversion processes). The methane in the methane-containing feed may therefore be derived from a renewable carbon source. Other possible components of methane-containing feeds include effluents of industrial processes such as steel manufacturing processes or non-ferrous product manufacturing processes. Further possible components include effluents of petroleum refining processes, electric power production processes, chemical (e.g., methanol) production processes, and coke manufacturing processes.

Representative processes comprise providing a methane-containing feed as described herein to a methane conversion reactor operating under methane conversion conditions to obtain a product (e.g., an effluent of the methane conversion reactor), comprising $C_2^+$ hydrocarbons as described herein. The methane-containing feed may be provided to the reactor according to a batchwise process, for example in which the reactor is first charged with a fixed amount (batch) of the methane-containing feed, and optionally a catalyst as described herein. The reactor contents may then be maintained under suitable methane conversion conditions and for a suitable residence time as described herein, following which time the product is removed. Preferably, however, the methane-containing feed is provided to the methane conversion reactor, while maintained under suitable methane conversion conditions as described herein, as a continuous flow (e.g., as a gas feed stream), and the product is removed from this reactor as a continuous flow (e.g., as a gas product stream), with the average gas residence time corresponding a suitable residence time as described herein. Such a continuous process, relative to a batchwise process, is generally more economically operable on a large scale, and in addition allows for recycle of valuable components of the product, and in particular hydrogen and unconverted methane.

Whether processes described herein are practiced batchwise or continuously, aspects of the invention relate to the discovery of particular methane conversion conditions, and combinations of conditions, leading to advantageous performance parameters such as a methane conversion, selectivity to $C_2^+$ hydrocarbons, or yield of $C_2^+$ hydrocarbons as described herein (with the yield resulting from the combination of conversion and selectivity). In this context, the term "$C_2^+$ hydrocarbons" refers to all to hydrocarbons having two or more carbon atoms, although in more particular embodiments, "$C_2^+$ hydrocarbons" may be replaced with any of the groups of hydrocarbons (e.g., $C_2$-$C_7$ hydrocarbons) and/or any of the individual hydrocarbons or combinations of any of the individual hydrocarbons noted above. The $C_2^+$ hydrocarbons, according to any of these embodiments, are preferably obtained in the product from the conversion of methane.

In this regard, particular methane conversion conditions, under which the methane conversion reactor operates, such as to achieve performance parameters as described herein, may include relatively low pressures and/or relatively low residence times. Representative absolute pressures are generally less than about 1 megapascal (MPa), for example from about 0.01 MPa to about 1 MPa, from about 0.01 MPa to about 0.5 MPa, or from about 0.01 MPa to about 0.2 MPa. In some embodiments, the absolute pressure is in a range from near atmospheric pressure, or about 0.1 MPa, to about 1 MPa, such as from about 0.1 MPa to about 0.8 MPa, from about 0.1 MPa to about 0.5 MPa, from about 0.4 MPa to about 0.6 MPa, from about 0.1 MPa to about 0.2 MPa, or from about 0.1 MPa to about 0.15 MPa. For example, according to particular embodiments, an absolute operating pressure of near atmospheric pressure or slightly above atmospheric pressure (e.g., in a range from about 0.1 MPa to about 0.25 MPa) may be associated with obtaining high yields of $C_2^+$ hydrocarbons, and $C_2$-$C_7$ hydrocarbons in particular, in the product. According to other embodiments, the methane conversion conditions may include a pressure that is below atmospheric pressure, such as an absolute pressure from about 1 kPa to about 100 kPa, from about 10 kPa to about 75 kPa, or from about 10 kPa to about 50 kPa. Such pressures may be obtained, for example, using a vacuum system and may be particularly advantageous in combination with other methane conversion conditions as described herein.

With respect to the methane conversion condition of residence time, optionally in combination with an absolute pressure within any of the ranges given above, in particular embodiments relatively low residence time is advantageous in terms of inhibiting coking, or the formation of condensed, solid carbonaceous material (coke) from methane that necessarily results in a yield loss in desired $C_2^+$ hydrocarbons as described above (e.g., small molecules such as the $C_2$ hydrocarbons ethane, ethylene, and acetylene and/or aromatic hydrocarbons). In embodiments in which the methane conversion reactor contains a catalyst, coke formation on the catalyst surface can lead to its deactivation by hindering or blocking access of methane to the methane conversion active metal(s) of the catalyst. Advantageous residence times, in terms of achieving sufficient conversion of methane in the absence of excessive coke formation, are generally less than about 60 seconds, such as from about 1 second to about 60 seconds, from about 2 seconds to about 60 seconds, from about 5 seconds to about 60 seconds, or from about 10 seconds to about 60 seconds. Other representative ranges of residence times in this regard are from about 1 second to about 30 seconds, from about 1 second to about 15 seconds, from about 1 second to about 10 seconds, from about 5 seconds to about 15 seconds, or from about 7 seconds to about 15 seconds.

As is understood in the art, in the case of continuous processes, residence time refers to the average time in which the reaction mixture in the methane conversion reactor, which may comprise molecules of the methane-containing feed, of the product, and/or of any intermediates formed, resides in the reactor volume. For purposes of this disclosure and for ease of calculation, the term "residence time," refers to the volume of the methane conversion reactor divided by volumetric flow rate of the methane-containing feed to this reactor, with the volumetric flow rate being determined under the methane conversion conditions used, including the absolute pressure and temperature. In embodiments in which the methane conversion reactor contains a catalyst, the term "residence time" is as described above, but with the volume of the catalyst bed substituting for the volume of the methane conversion reactor. A further methane conversion condition related to residence time (or, more accurately, related to the inverse of residence time) is the gas hourly space velocity (GHSV), which is calculated by dividing the hourly volumetric flow rate of the methane-containing feed, determined under standard conditions, by the reactor volume, or otherwise by the volume of the catalyst bed in embodiments in which the methane conversion reactor contains a catalyst. The GHSV therefore provides a measure of the equivalent number of reactor volumes, or catalyst bed volumes, of the methane-containing feed that are processed per hour. Representative values of the methane conversion condition of GHSV, optionally in combination with an absolute pressure within any of the ranges given above and/or with a residence time within any of the ranges given above, are generally from about 10 $hr^{-1}$ to about 10,000 $hr^{-1}$, typically from about 50 $hr^{-1}$ to about 5,000 $hr^{-1}$, and often from about 100 $hr^{-1}$ to about 4,500 $hr^{-1}$, such as from about 150 $hr^{-1}$ to about 4,000 $hr^{-1}$.

With respect to temperature, this methane conversion condition can refer to the temperature (or average temperature) maintained within the methane conversion reactor or within a catalyst bed (if catalyst is used) contained in this reactor. Representative temperatures, optionally in combination with an absolute pressure within any of the ranges given above, a residence time within any of the ranges give above, and/or a GHS V within any of the ranges given above, are generally from about 750° C. to about 2000° C., typically from about 800° C. to about 1500° C., and often from about 900° C. to about 1275° C., with a range from about 1000° C. to about 1200° C. being preferred.

As noted above, particular aspects of the invention relate to the finding that the presence of hydrogen in the reaction system can be beneficial in terms of promoting the desired conversion of methane to higher hydrocarbons. In fact, the deliberate introduction of hydrogen to this system, such that the amount present in the reactor may exceed that obtained merely from the dehydrogenation of methane, can lead to an improvement in performance parameters (e.g., methane conversion and/or yields of $C_2^+$ hydrocarbons). This is despite an expectation, in view of the reaction chemistry alone, that the addition of a component produced by the reaction would be unfavorable from an equilibrium standpoint. According to some embodiments, hydrogen may be present in the methane-containing feed, for example such that a representative $H_2$:$CH_4$ molar ratio in this feed may range generally from about 0.1 to about 10, typically from about 0.5 to about 5, and often from about 0.5 to about 3. Alternatively, or in combination, hydrogen and methane may constitute all or substantially all of the methane-containing feed. For example, in representative embodiments, this feed may comprise at least about 80 vol-%, at least about 90 vol-%, at least about 95 vol-%, or at least about 99 vol-%, of hydrogen and methane in combination. The $H_2$:$CH_4$ molar ratio, and/or combined volume percentage of hydrogen and methane, in the methane-containing feed provided to the methane conversion reactor, may therefore constitute further methane conversion condition(s) under which the reactor is operated, optionally in combination with one or more of an absolute pressure, a residence time, a GHSV, and/or a temperature within respective ranges as described above.

In addition, to the extent that reaction kinetics and equilibrium are influenced by the concentration of hydrogen in the methane conversion reactor, additional methane conversion conditions of interest include the hydrogen content, in terms of its volume percentage, in this reactor, and the hydrogen partial pressure, in terms of the product of its volume percentage and the absolute pressure, in this reactor. In representative embodiments, for example, the hydrogen content in the methane conversion reactor may be at least about 10 vol-% (e.g., from about 10 vol-% to about 85 vol-%), at least about 20 vol-% (e.g., from about 20 vol-% to about 75 vol-%), or at least about 25 vol-% (e.g., from about 25 vol-% to about 50 vol-%). Alternatively, or in combination, the hydrogen partial pressure in the methane conversion reactor may be at least about 1 kilopascal (kPa) (e.g., from about 1 kPa to about 1000 kPa), at least about 10 kPa (e.g., from about 10 kPa to about 500 kPa), or at least about 100 kPa (e.g., from about 100 kPa to about 300 kPa). The hydrogen content and/or hydrogen partial pressure in the methane conversion reactor may therefore constitute further methane conversion condition(s) under which the reactor is operated, optionally in combination with one or both of an $H_2$:$CH_4$ molar ratio and a combined volume percentage of hydrogen and methane, in the methane-containing feed provided to the methane conversion reactor, within the respective ranges described above, and/or optionally in combination with one or more of an absolute pressure, a residence time, a GHSV, and/or a temperature within respective ranges as described above.

Processes described herein for converting methane to $C_2^+$ hydrocarbons, including processes operating under one or more methane conversion conditions as described above (i.e., with these one or more conditions being within respective ranges given above), may be performed catalytically, meaning that the methane conversion reactor contains a catalyst. Alternatively, these processes may be performed non-catalytically, or in the absence of any catalyst in this reactor. If used, suitable catalysts include solid catalysts in various forms (e.g., a bed comprising spherical or cylindrical particles of catalyst, or comprising a larger catalyst monolith) that are effective for providing the requisite contacting and pressure drop characteristics, which depend on active metal loading, support porosity and dimensions, and other properties that would be recognized and discernable to one skilled in the art, with knowledge of the present specification. Representative catalysts may comprise one or more methane conversion active metals (i.e., one or more metals that, in the environment of the methane conversion reactor, effectively "activate" methane by lowering the activation energy of its reaction to form one or more $C_2^+$ hydrocarbons as described above). The one or more methane conversion active metals may, for example, be selected from the group consisting of Fe, Cr, Mn, V, Mo, and W. The one or more metals may be present in elemental (0 oxidation state) form or in the form of a compound (e.g., an oxide, a hydride, a sulfide, a nitride, or other form), or, in the case of two or more metals, these may be present in differing forms. Regardless of the form(s) of the metal(s), any one, or any combination, of these methane conversion active metal(s) may be present in the catalyst in an amount, or combined amount, from about 0.1 wt-% to about 10 wt-%, such as from about 0.3 wt-% to about 8 wt-% or from about 0.3 wt-% to about 5 wt-%. The methane conversion active metal(s) may be supported on, i.e., may be deposited on the surface of and/or within pores of, a suitable support material that is refractory to the conditions in the methane conversion reactor. Representative support materials include inorganic metal oxides such as alumina, silica, titania, zirconia, magnesia, ceria, and combinations of these. The one or more methane conversion active metal(s), or their metallic form(s), in combination with the support material(s), may represent substantially the entire weight of the catalyst, for example at least about 95 wt-%, at least about 98 wt-%, or at least about 99 wt-%, of the catalyst weight.

One or a combination of the methane conversion conditions described above may be used, optionally in conjunction with a catalyst as described above, to achieve important performance parameters, for example those predicted from an approach involving the coupling of gas phase and heterogeneous reaction models, with such models having been validated based on experimental testing. Of significant interest in terms of such performance parameters are methane conversion, selectivity to $C_2^+$ hydrocarbons, yield of $C_2^+$ hydrocarbons, and volume percentage of $C_2^+$ hydrocarbons in the product (or effluent of the methane conversion reactor). As noted above, "$C_2^+$ hydrocarbons" refers to all to hydrocarbons having two or more carbon atoms. In the case of performance parameters being described with respect to "$C_2^+$ hydrocarbons," these may likewise be achieved, in more particular embodiments, with respect to any of the groups of hydrocarbons (e.g., $C_2$-$C_7$ hydrocarbons) and/or any of the individual hydrocarbons or combinations of any of the individual hydrocarbons noted above. For example, in some embodiments, particularly in the context of characterizing performance of the process, ranges of selectivities, yields, and volume percentages as described herein may refer to those of (i) the $C_2$ hydrocarbons ethane, ethylene, and acetylene, (ii) single ring aromatic hydrocarbons, (iii) fused, 2-ring hydrocarbons having at least one aromatic ring, (iv) fused, 3-ring hydrocarbons having at least one aromatic ring, (v) the combination of (ii), (iii), and (iv) above, or (iv) all $C_2^+$ hydrocarbons.

The term "conversion" refers to the conversion of methane in the methane-containing feed, over a single pass through the methane conversion (i.e., the single-pass conversion). This can be calculated, for example, by determining the weight, or the steady-state weight per unit time in the case of continuous flow processes, of methane in both the methane-containing feed and the product ($WCH_{4feed}$ and $WCH_{4prod}$), such that the conversion has a value of $1-(WCH_{4prod}/WCH_{4feed})$, expressed as a percentage. The selectivity to one or more $C_2^+$ hydrocarbons may be calculated by determining the weight, or the steady-state weight per unit time, of the one or more $C_2^+$ hydrocarbons that have been produced, i.e., weight present in the product that is absent in the methane-containing feed ($WC_2{}^+{}_{prod}-WC_2{}^+{}_{feed}$), and then determining the weight, or steady-state weight per unit time, of the total $C_2^+$ hydrocarbons that have been produced (i.e., excluding the weight of hydrocarbons in the feed that remain unconverted in the product) ($WTOTC_2{}^+{}_{prod}-WTOTC_2{}^+{}_{feed}$), such that the selectivity has a value of ($WC_2{}^+{}_{prod}-WC_2{}^+{}_{feed}$) ($WTOTC_2{}^+{}_{prod}-WTOTC_2{}^+{}_{feed}$), expressed as a percentage. The yield of one or more $C_2^+$ hydrocarbons may be determined as the weight, or steady-state weight per unit time, of the one or more $C_2^+$ hydrocarbons produced, divided by the weight, or steady-state weight per unit time, of methane in the methane-containing feed (i.e., the weight of methane that could theoretically be converted to yield the one or more $C_2^+$ hydrocarbons), expressed as a percentage.

According to particular embodiments of the invention, the conversion of methane may be at least about 15 wt-% (e.g., from about 15 wt-% to about 98 wt-%), at least about 25 wt-% (e.g., from about 25 wt-% to about 95 wt-%), or at least about 45 wt-% (e.g., from about 45 wt-% to about 90 wt-%). Independently, or otherwise in combination with a conversion of methane within any of the above ranges, the selectivity (i) to $C_2$ hydrocarbons may be at least about 35 wt-% (e.g., from about 35 wt-% to about 75 wt-%) or at least about 45 wt-% (e.g., from about 45 wt-% to about 65 wt-%), (ii) to single ring aromatic hydrocarbons may be at least about 45 wt-% (e.g., from about 45 wt-% to about 85 wt-%) or at least about 55 wt-% (e.g., from about 55 wt-% to about 75 wt-%), (iii) to fused, 2-ring hydrocarbons may be at least about 10 wt-% (e.g., from about 10 wt-% to about 50 wt-%) or at least about 20 wt-% (e.g., from about 20 wt-% to about 40 wt-%), (iv) to fused, 3-ring hydrocarbons may be at least about 10 wt-% (e.g., from about 10 wt-% to about 40 wt-%) or at least about 15 wt-% (e.g., from about 15 wt-% to about 30 wt-%), (v) to the combination of (ii), (iii), and (iv) above may be at least about 50 wt-% (e.g., from about 50 wt-% to about 95 wt-%) or at least about 60 wt-% (e.g., from about 60 wt-% to about 90 wt-%), and/or (vi) to all $C_2^+$ hydrocarbons may be at least about 85 wt-% (e.g., from about 85 wt-% to about 100 wt-%) or at least about 90 wt-% (e.g., from about 90 wt-% to about 99 wt-%).

Independently, or otherwise in combination with a conversion of methane within any of the above ranges and/or one or more selectivities within any of the above, respective ranges, the yield (i) of $C_2$ hydrocarbons may be at least about 10 wt-% (e.g., from about 10 wt-% to about 50 wt-%) or at least about 20 wt-% (e.g., from about 20 wt-% to about 40 wt-%), (ii) of single ring aromatic hydrocarbons may be at least about 25 wt-% (e.g., from about 25 wt-% to about 55 wt-%) or at least about 30 wt-% (e.g., from about 30 wt-% to about 45 wt-%), (iii) of fused, 2-ring hydrocarbons may be at least about 5 wt-% (e.g., from about 5 wt-% to about 45 wt-%) or at least about 10 wt-% (e.g., from about 10 wt-% to about 40 wt-%), (iv) of fused, 3-ring hydrocarbons may be at least about 10 wt-% (e.g., from about 10 wt-% to about 45 wt-%) or at least about 15 wt-% (e.g., from about 15 wt-% to about 35 wt-%), (v) of the combination of (ii), (iii) and (iv) above may be at least about 30 wt-% (e.g., from about 30 wt-% to about 75 wt-%) or at least about 40 wt-% (e.g., from about 40 wt-% to about 65 wt-%), and/or (vi) of all $C_2^+$ hydrocarbons may be at least about 45 wt-% (e.g., from about 45 wt-% to about 90 wt-%) or at least about 50 wt-% (e.g., from about 50 wt-% to about 85 wt-%).

Advantageously, processes for the conversion of methane may be carried out with methane conversion conditions and/or performance parameters as described herein, and further with a small or even negligible loss of carbon present in the methane to undesired coke. For example, methane conversion within ranges as described herein may be obtained with the selectivity to, or yield of, coke being less than about 3 wt-%, less than about 1 wt-%, or less than about 0.1 wt-%.

Independently, or otherwise in combination with a conversion of methane within any of the above ranges; one or more selectivities within any of the above, respective ranges; and/or one or more yields within any of the above, respective ranges, the product may comprise (i) $C_2$ hydrocarbons in an amount of at least about 20 vol-% (e.g., from about vol-% to about 90 vol-%) or at least about 45 vol-% (e.g., from about 45 vol-% to about 80 vol-%), (ii) single ring aromatic hydrocarbons in an amount of at least about 10 vol-% (e.g., from about 10 vol-% to about 40 vol-%) or at least about 15 vol-% (e.g., from about 15 vol-% to about 30 vol-%), (iii) of fused, 2-ring hydrocarbons in an amount of at least about 3 vol-% (e.g., from about 3 vol-% to about 25 vol-%) or at least about 5 vol-% (e.g., from about 5 vol-% to about 15 vol-%), (iv) fused, 3-ring hydrocarbons in an amount of at least about 3 vol-% (e.g., from about 3 vol-% to about 25 vol-%) or at least about 5 vol-% (e.g., from about 5 vol-% to about 20 vol-%), (v) the combination of (ii), (iii), and (iv) in an amount of at least about 35 vol-% (e.g., from about 35 vol-% to about 75 vol-%) or at least about 40 vol-% (e.g., from about 40 vol-% to about 65 vol-%), and/or (vi) all $C_2^+$ hydrocarbons in an amount of at least about 55 vol-% (e.g., from about 55 vol-% to about 98 vol-%) or at least about 70 vol-% (e.g., from about 70 vol-% to about 95 vol-%). These volume percentages are based on the product being completely in the gas phase, despite the potential of the product to contain compounds (e.g., aromatic hydrocarbons) that are liquid under ambient conditions.

As noted above, the performance parameters of conversion, selectivity, and/or yield may be determined on a "per-pass" or "once-through" basis, according to the total material introduced to the methane conversion reactor and the total material withdrawn from this reactor. Often, in view of economic considerations and particularly on a larger (e.g., commercial) scale, representative processes may operate by separating and recycling hydrogen and unconverted methane, from the remainder of the product or effluent of the methane conversion reactor (e.g., from a liquid comprising desired $C_2^+$ hydrocarbons such as aromatic hydrocarbons).

Separation may involve condensing the product to provide a liquid that is enriched, relative to the product, in desired $C_2^+$ hydrocarbons, as well as a vapor that is enriched, relative to the product, in hydrogen and unconverted methane, and optionally also enriched in $C_2$ hydrocarbons. The condensing may be performed by simply cooling the product to temperatures characteristic of cooling water, or to lower temperatures using a chiller or chilled adsorber. The condensing may involve a single vapor-liquid equilibrium stage of separation, for example by being performed in a flash drum, or otherwise multiple vapor-liquid equilibrium stages of separation in a single vessel (e.g., in the case of a stripper) or multiple vessels, such as in the case of a secondary knockout drum for removing $C_2^+$ hydrocarbons that may be carried (e.g., by entrainment) into a vapor phase of a primary flash drum. Alternative to, or in combination with, the use of a secondary knockout drum, such entrainment may be reduced using a suitable coalescer in an upper section of a primary flash drum.

In the case of separation and recycle, the performance parameters of conversion, selectivity, and/or yield may be determined on an "overall" basis, according to (i) the net material introduced to the overall process, and excluding from the total material introduced to the methane conversion reactor a recycle portion that is co-introduced to this reactor with the net material, and (ii) the net material withdrawn from the overall process, and excluding from the total material withdrawn from the methane conversion reactor a recycle portion that is co-withdrawn from this reactor with the net material and re-introduced to this reactor, such as co-introduced with the net material introduced. In the case of recycle operation, therefore, the methane-containing feed may include fresh methane in a fresh or make-up feed portion and recycle methane in a recycle portion, with the combination of these portions representing the methane-containing feed. Optionally, the recycle portion may constitute a substantial part of the recycle gas, with a minor part of the recycle gas being vented to prevent the accumulation of undesired impurities (e.g., non-condensable gases such as nitrogen) entering the recycle loop in minute quantities in the fresh or make-up feed portion.

By recycling unconverted methane, the overall conversion may considerably exceed the per-pass conversion. For example, as the extent of recycling increases, and approaches the condition of unconverted methane being recycled to extinction, the overall conversion approaches 100% (regardless of the per-pass conversion), and in this case the overall yield approaches the overall selectivity. In view of the present disclosure, those skilled in the art will appreciate the economic tradeoffs associated with increased product value due to increased yields, offset by increased costs due to increased recycle requirements. To the extent that processes are described herein in which unconverted methane may be recycled, according to particular embodiments the ranges of selectivities described above may alternatively be considered ranges of product yields.

The following examples are set forth as representative of the present invention. These examples are not to be construed as limiting the scope of the invention as other equivalent embodiments will be apparent in view of the present disclosure and appended claims.

EXAMPLE 1

Figure 2:
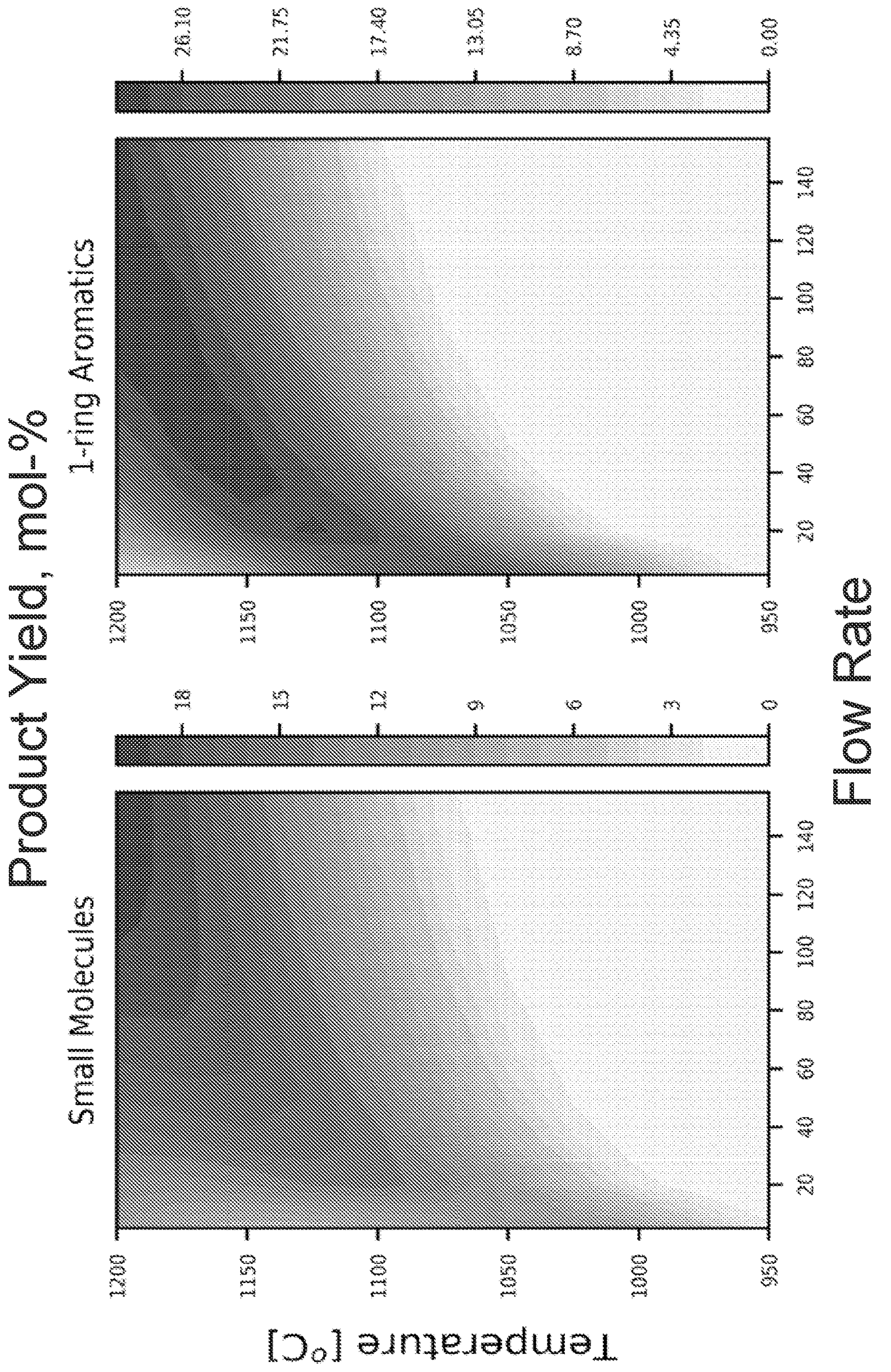
FIG. 2 depicts the product yields, in terms of $C_2$ hydrocarbons and single ring aromatic hydrocarbons, as a function of both reaction temperature and flow rate.

Microkinetic computer modelling was performed to simulate an experiment for conducting the gas phase conversion of methane to $C_2^+$ hydrocarbons. According to this modelling, the following procedures and methane conversion conditions were simulated: A reactor vessel was heated to a temperature of about 1200° C. and maintained at an absolute pressure of about 6 atmospheres (about 0.6 MPa). A stream of methane gas was then passed through this heated and pressurized reaction vessel at a flow rate of about 20 cc/min. The residence time of this feed in the pressurized and heated reaction vessel was between 8 to 10 seconds. The numerical simulation also included a determination of performance in terms of methane conversion and product yields over a range of flow rates and temperatures, based on the calculated composition of the gaseous mixture from the reactor outlet. Specifically, the simulated product contained $C_2$ hydrocarbon (ethylene, ethane, acetylene etc.) and higher hydrocarbons, including aromatic hydrocarbons (benzene, toluene, ethynyibenzene, naphthalene, indene, and acenaphthylene). The simulated conversion of methane as a function of both reaction temperature and flow rate is shown in FIG. 1, whereas the simulated product yields, in tetras of $C_2$ hydrocarbons and single ring aromatic hydrocarbons as a function of these variables is shown in FIG. 2. From the results of the modelling, the methane conversion was highest at a flow rate of about 20 cc/min and at a temperature of about 1200° C. In addition, conversion of methane to small molecules ($C_2$ hydrocarbons) was most efficient (about 20%) at temperatures of about 1200° C. and at a flow rate of about 140 cc/min. Similarly, conversion of methane to single ring aromatics was most efficient at a flow rate of from about 40 cc/min to about 140 cc/min and at a temperature of about 1150° C. to about 1200° C.

Figure 3:
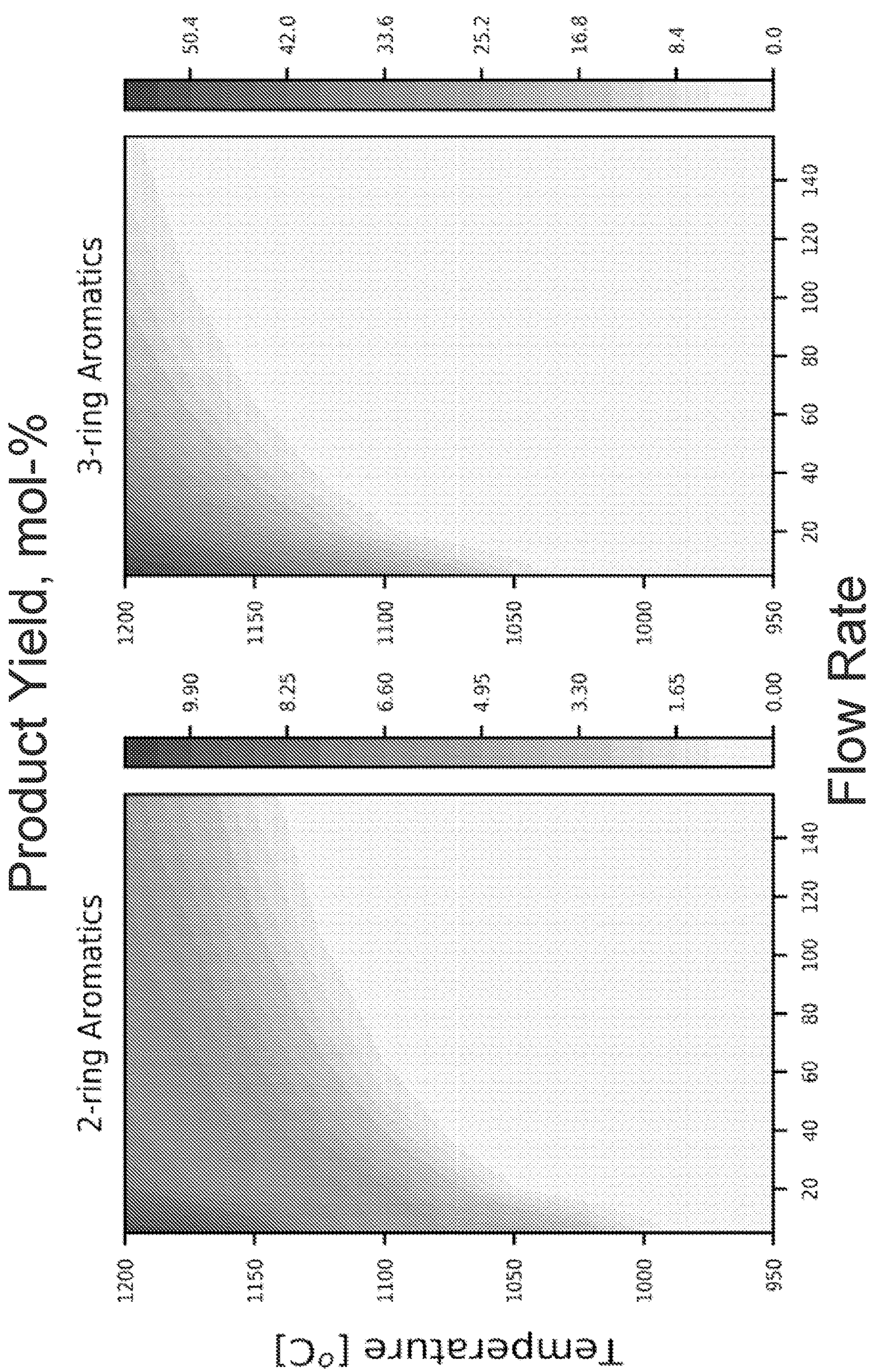
FIG. 3 depicts the product yields, in terms of fused, 2-ring aromatic hydrocarbons and fused, 3-ring aromatic hydrocarbons, as a function of both reaction temperature and flow rate.

The simulated product yields, in terms of fused, 2-ring aromatic hydrocarbons and fused, 3-ring aromatic hydrocarbons as a function of both reaction temperature and flow rate is shown in FIG. 3. From the results of the modelling studies, conversion of methane to these $C_2^+$ hydrocarbons was most efficient at a flow rate of from about 5 cc/min and at a temperature of about 1150° C. to about 1200° C.

EXAMPLE 2

Microkinetic computer modelling was performed to simulate another experiment for conducting the gas phase conversion of methane to $C_2^+$ hydrocarbons. According to this modelling, the following procedures and methane conversion conditions were simulated: A reactor vessel was heated to a temperature of about 1200° C. and maintained at an absolute pressure of about 6 atmospheres (about 0.6 MPa). The reactor vessel in this example contained a catalyst having iron dispersed on a silica support ($FeSiO_2$). A stream of methane gas was then passed through this heated and pressurized reaction vessel at a flow rate of about 20 cc/min. The residence time of this feed in the pressurized and heated reaction vessel was between 8 to 10 seconds. The numerical simulation also included a determination of performance in terms of methane conversion and product yields over a range of flow rates and temperatures, based on the calculated composition of the gaseous mixture from the reactor outlet. Specifically, the simulated product contained $C_2$ hydrocarbons (ethylene, ethane, acetylene etc.) and higher hydrocarbons, including aromatic hydrocarbons (benzene, toluene, ethynylbentene, naphthalene, indene, and acenaphthylene).

Figure 4A:
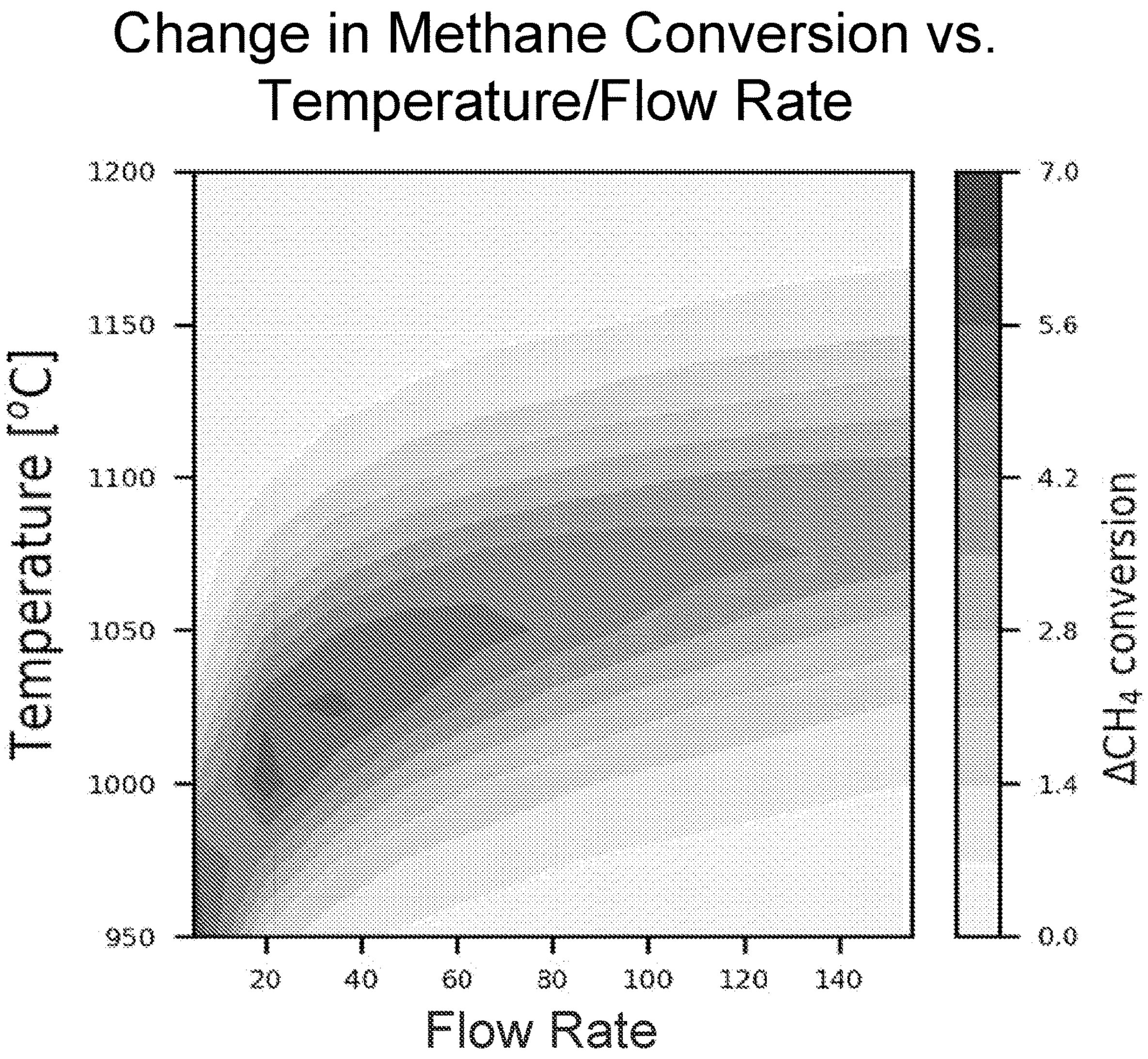
FIGS. 4A-4C depict the change in conversion of methane as a function of both reaction temperature and the following, additional methane conversion conditions: flow rate (FIG. 4A), residence time (FIG. 4B), gas hourly space velocity (FIG. 4C).
Figure 4B:
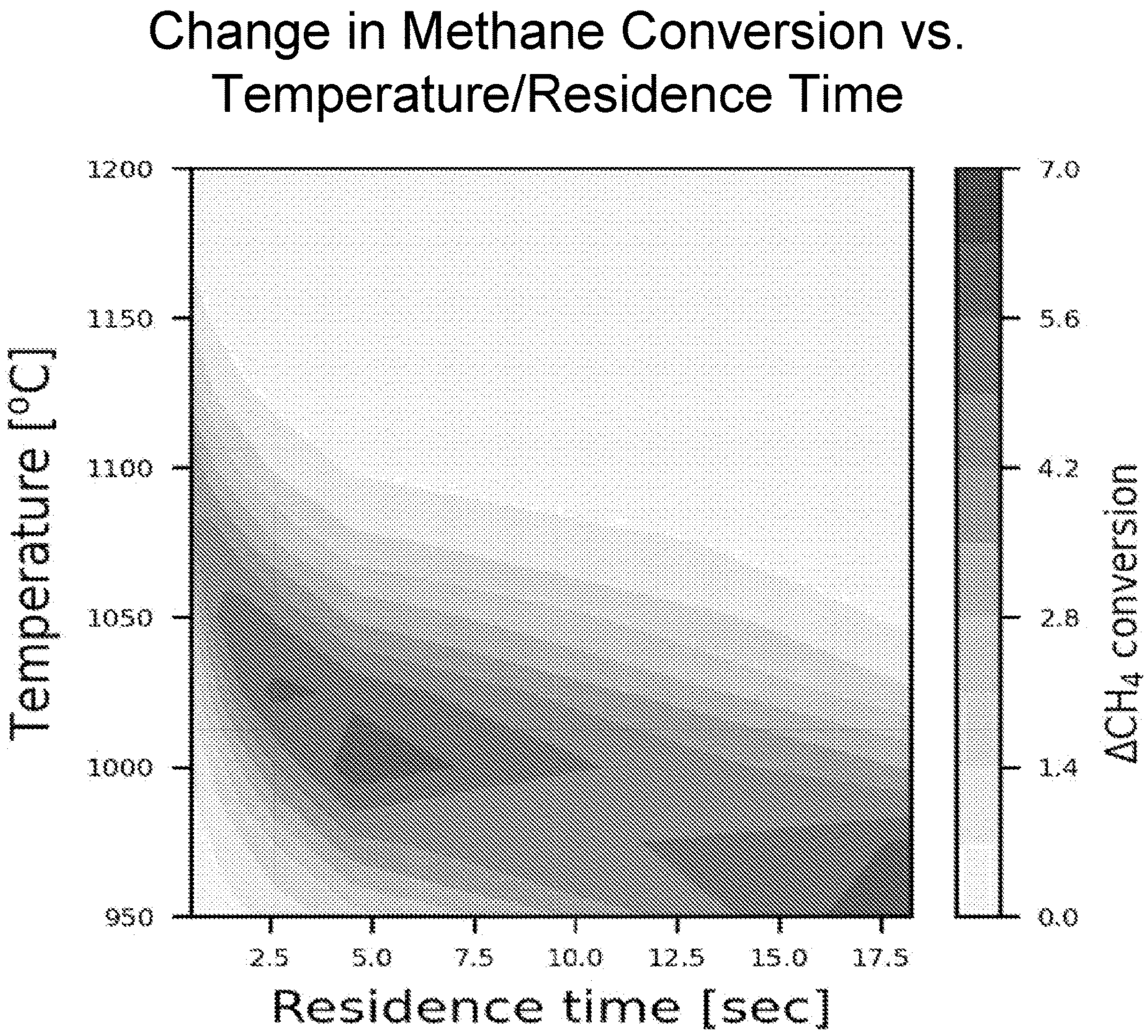
Figure 4C:
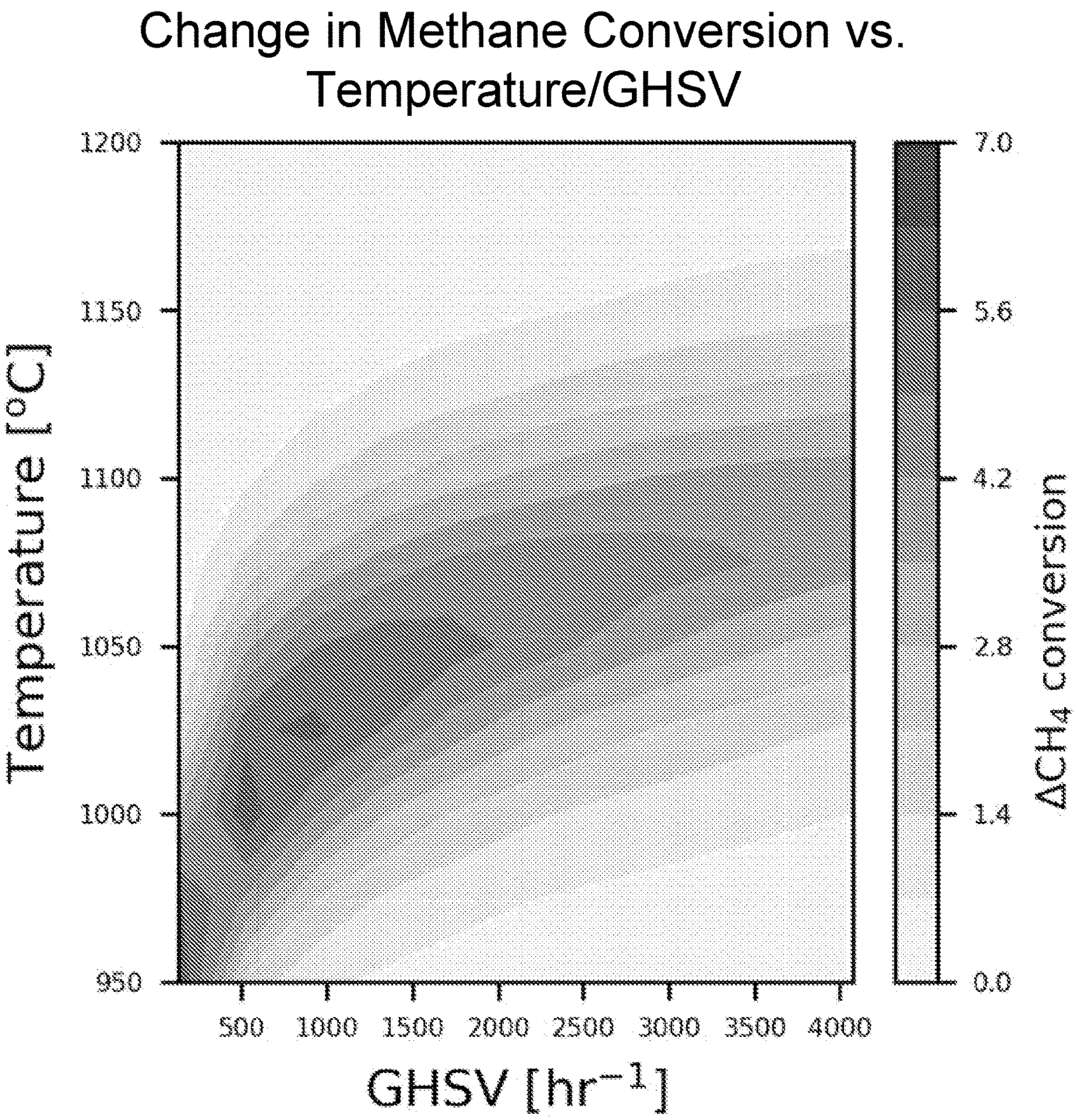

The simulated change in conversion of methane as a function of both reaction temperature and the following, additional methane conversion condition of (i) flow rate is shown in FIG. 4A, (ii) residence time is shown in FIG. 4B, and (iii) gas hourly space velocity (GHSV) is shown in FIG. 4C. As indicated in FIG. 4A, the simulated change in methane conversion was highest at a flow rate of about 20 cc/min and at a temperature of about 1000° C.

Figure 5A:
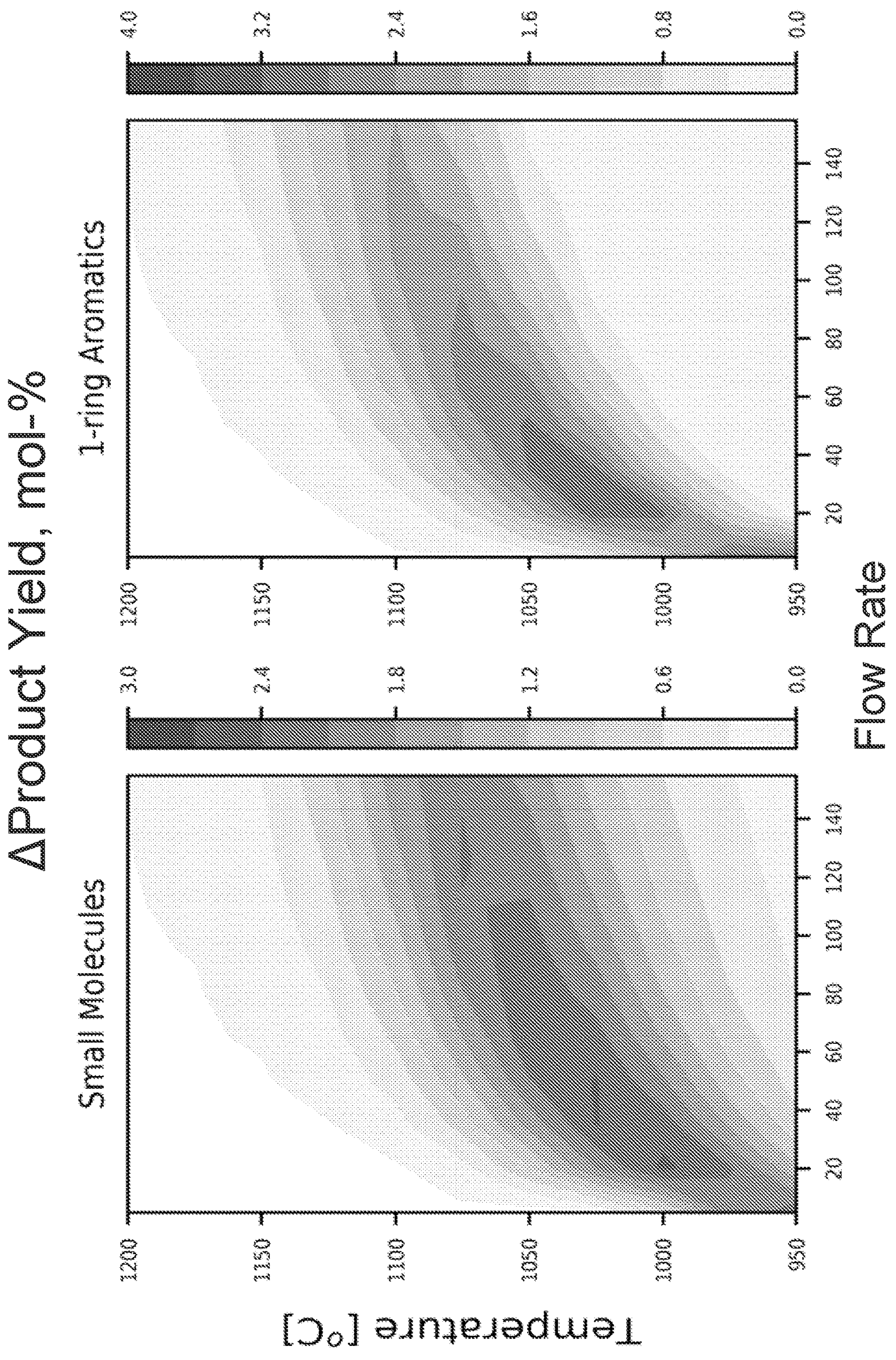
FIGS. 5A-5C depict the change in product yields, in terms of $C_2$ hydrocarbons and single ring aromatic hydrocarbons, as a function of both reaction temperature and the following, additional methane conversion conditions: flow rate (FIG. 5A), residence time (FIG. 5B), gas hourly space velocity (FIG. 5C).
Figure 5B:
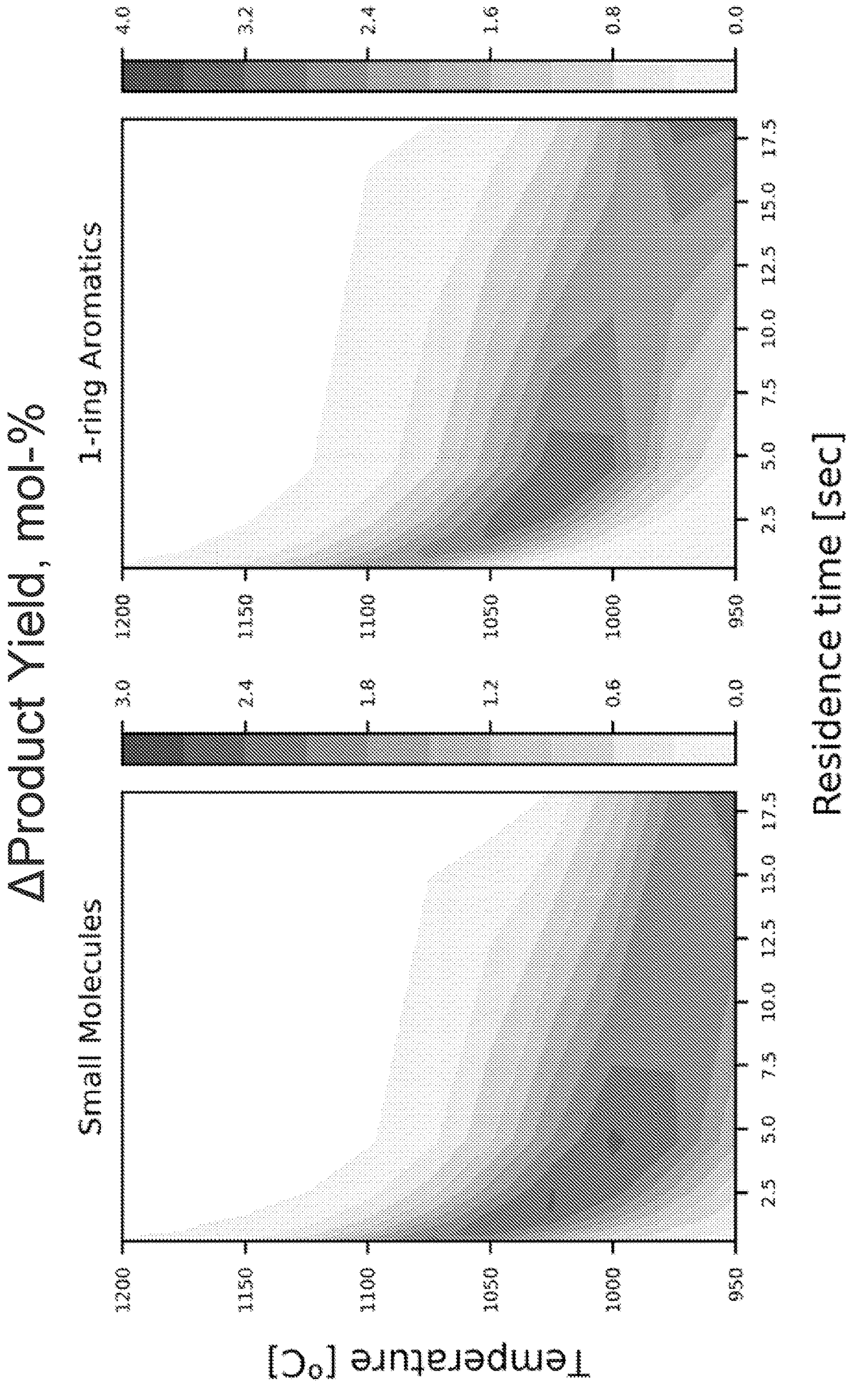
Figure 5C:
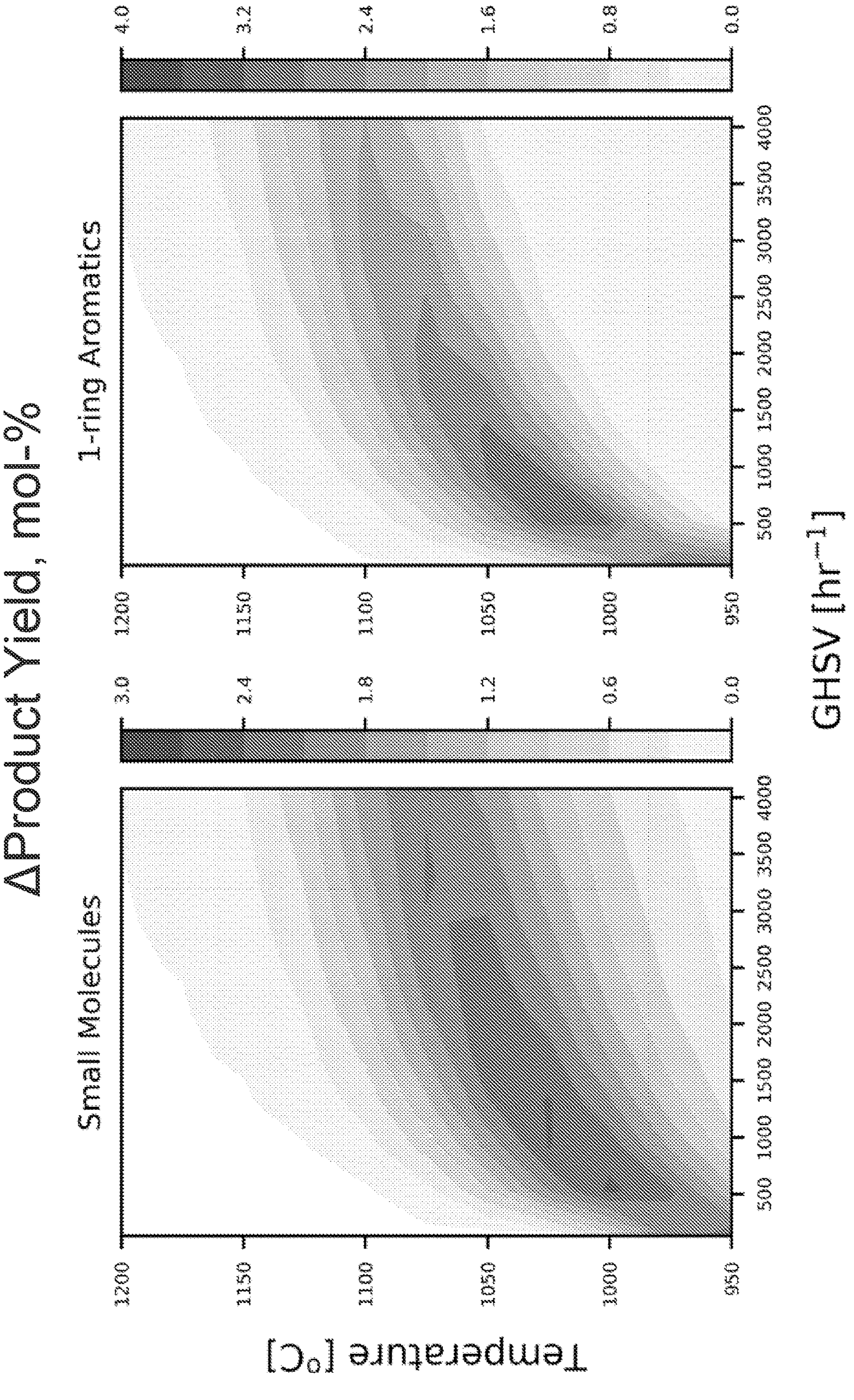

The simulated change in product yield, in terms of $C_2$ hydrocarbons and single ring aromatic hydrocarbons, as a function of both reaction temperature and the following, additional methane conversion condition of (i) flow rate is shown in FIG. 5A, (ii) residence time is shown in FIG. 5B, and (iii) gas hourly space velocity (GHSV) is shown in FIG. 5C. As indicated in FIG. 5A, the simulated methane conversion to $C_2$ hydrocarbons was most efficient at a temperature of about 1000° C. and at a flow rate of about 20 cc/min. Similarly, from the results of the modelling studies, the methane conversion to single ring aromatic hydrocarbons was most efficient at a temperature of about 1200° C. and a flow rate of about 20 cc/min.

Figure 6A:
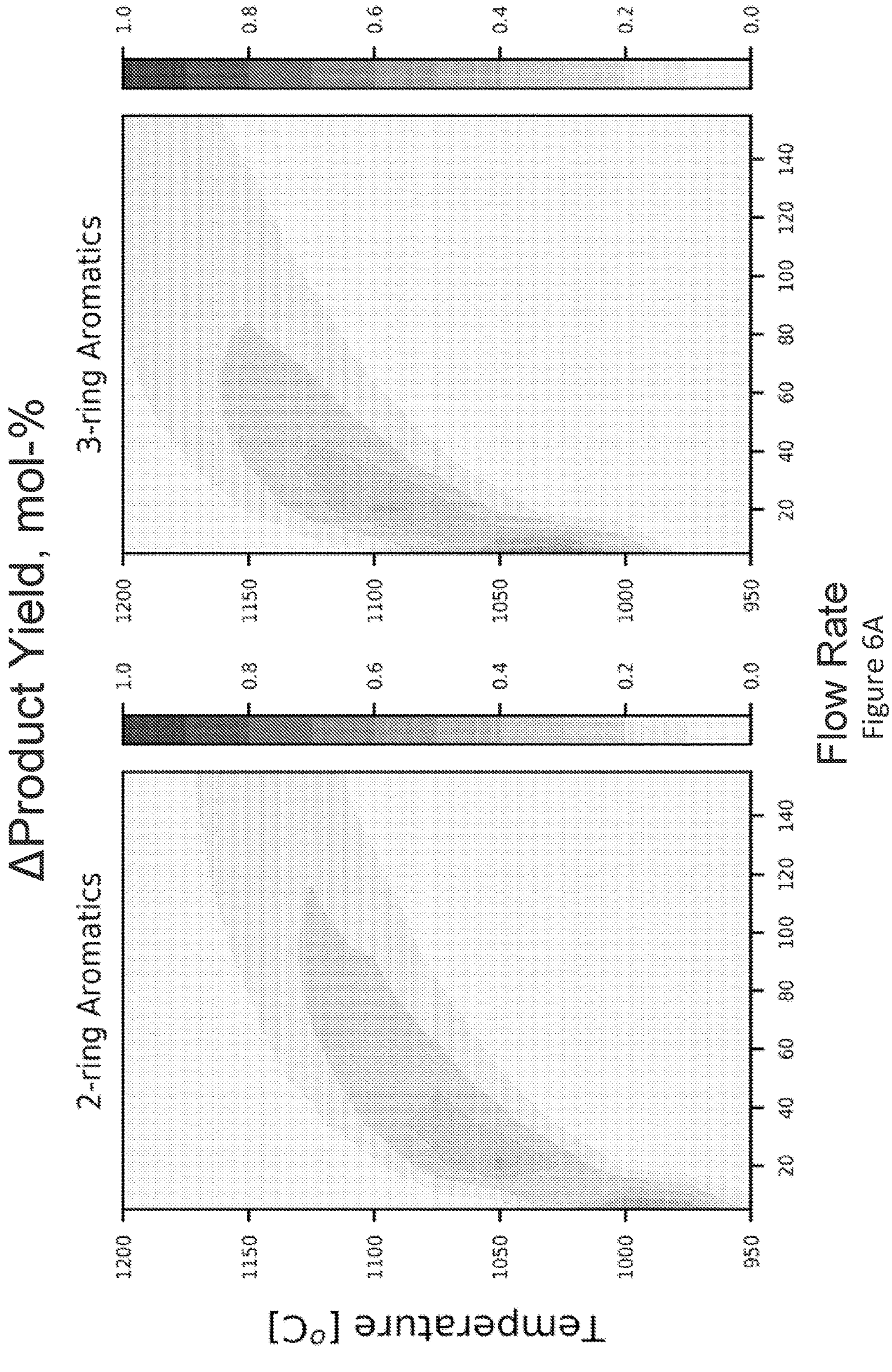
FIGS. 6A-6C depict the change in product yields, in terms of fused, 2-ring aromatic hydrocarbons and fused, 3-ring aromatic hydrocarbons, as a function of both reaction temperature and the following, additional methane conversion conditions: flow rate (FIG. 6A), residence time (FIG. 6B), gas hourly space velocity (FIG. 6C).
Figure 6B:
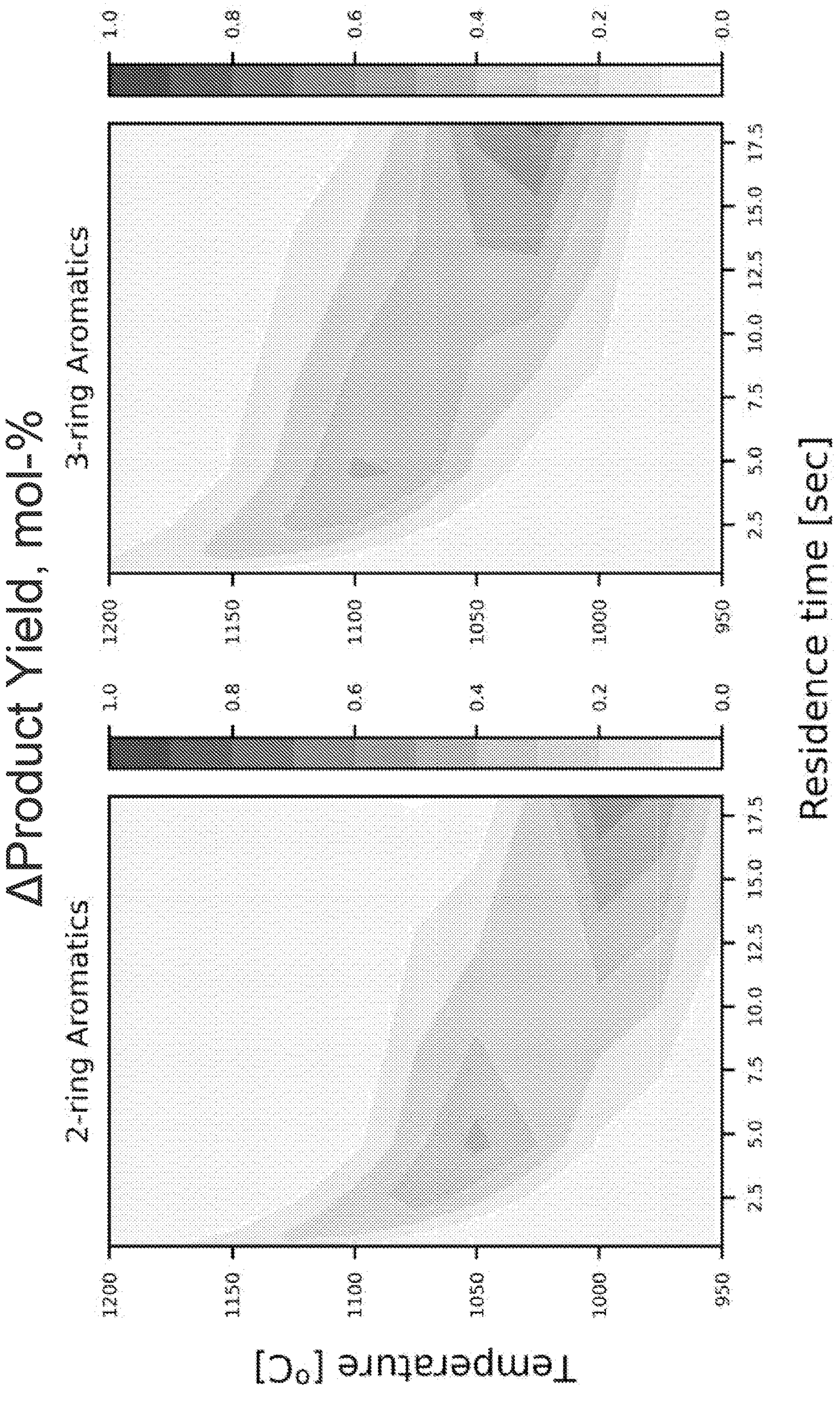
Figure 6C:
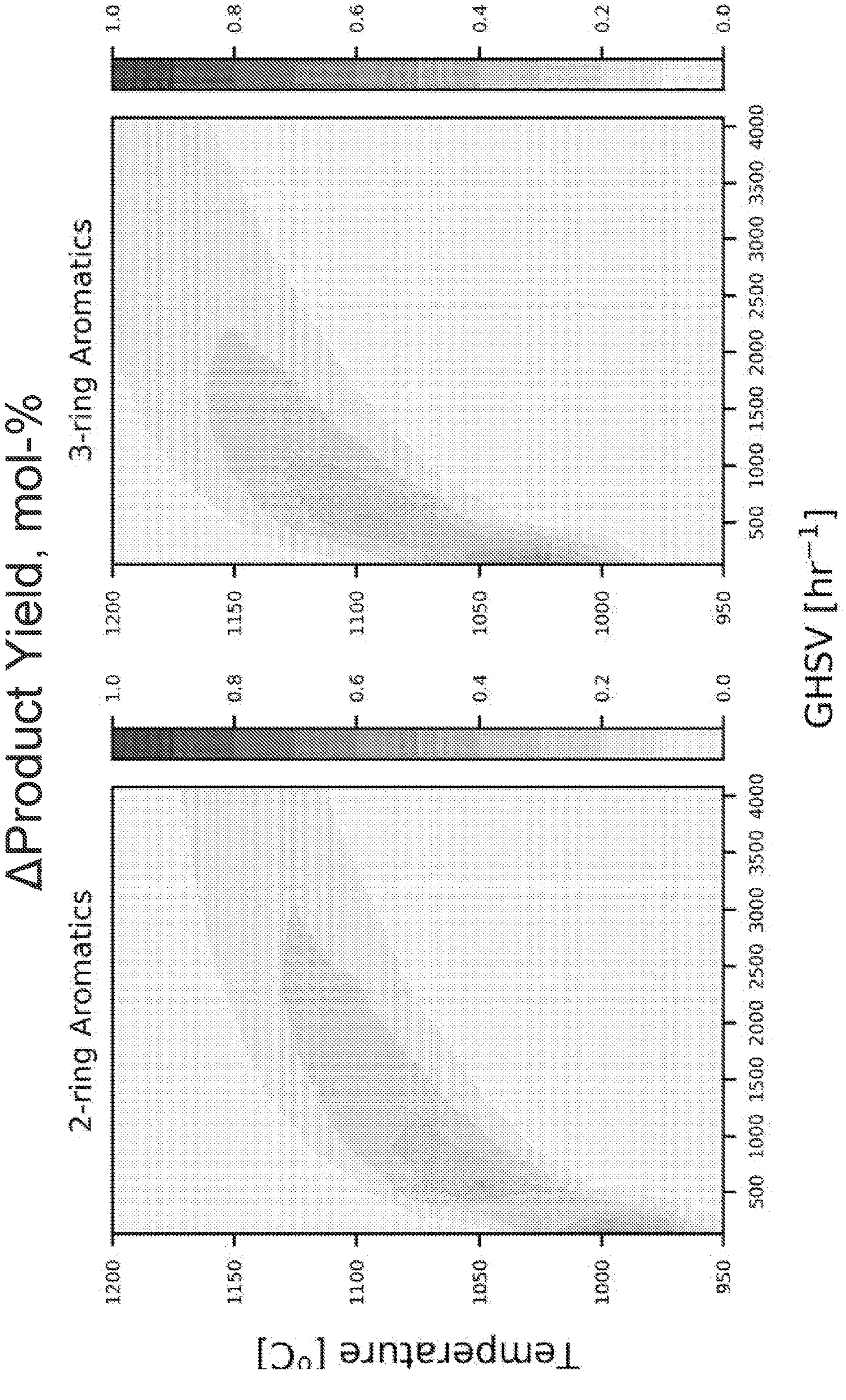

The simulated change in product yield, in terms of fused, 2-ring aromatic hydrocarbons and fused, 3-ring aromatic hydrocarbons, as a function of both reaction temperature and the following, additional methane conversion condition of (i) flow rate is shown in FIG. 6A, (ii) residence time is shown in FIG. 6B, and (iii) gas hourly space velocity (GHSV) is shown in FIG. 6C. As indicated in FIG. 6A, the simulated methane conversion to fused, 2-ring and 3-ring aromatics is most efficient at a flow rate of about 20 cc/min and at a temperature of about 1200° C.

Advantageously, based on results from the modelling studies, the conversion of methane could be performed in a stable manner, with only a minimal formation of coke that could otherwise reduce the activity of the catalyst. Suppression of coke formation could be achieved by maintaining certain methane conversion conditions, such as a residence time of less than 10 seconds (e.g., about 8-10 seconds) and/or a co-feed of hydrogen.

EXAMPLE 3

According to an experiment for conducting the gas phase conversion of methane to $C_2^+$ hydrocarbons, a reactor vessel (an alumina tube in this case) was heated to a temperature of about 1260° C., and maintained at an absolute pressure of 0.2 atmospheres (about 20 kPa absolute). A methane-containing feed consisting of methane and hydrogen gas with a 1:1 $H_2$:$CH_4$ molar ratio was then passed through this reactor vessel with a residence time of 4.8 seconds. The product, as a gaseous mixture, was collected from the reactor outlet, analyzed, and found to contain 61.2 vol-% $C_2$ hydrocarbons (ethylene, ethane, and acetylene) and 14.9 vol-% benzene and higher hydrocarbons, including multi-ring aromatic hydrocarbons. In this case, the methane conversion was 60.9 wt-%. This example demonstrated favorable performance parameters, particularly methane conversion and yields of desired $C_2^+$ hydrocarbons, under the tested methane conversion conditions that included the combination of the $H_2$:$CH_4$ molar ratio, pressure, residence time, and temperature as noted.

EXAMPLES 4-7

Examples 4-7 were performed as described with respect to Example 3. However, different methane conversion conditions of temperature (Temp.), absolute pressure (Pressure), residence time (TRes), and $H_2$:$CH_4$ molar ratio ($H_2$:$CH_4$) were tested, as summarized in the table below, which also provides the performance parameters of $C_2$ hydrocarbon content (Prod. $C_2$) and benzene and higher hydrocarbon content (Prod. $C_6^+$), as determined in the product, in addition to methane conversion ($XCH_4$).

Summary Table, Examples 4-7

| Example | Temp., ° C. | Pressure, kPa | TRes, sec | $H_2$:$CH_4$, molar | Prod. $C_2$, vol-% | Prod. $C_6^+$, vol-% | $XCH_4$, wt-% |
|---|---|---|---|---|---|---|---|
| 4 | 1075 | 100 | 5.1 | 0 | 20.3 | 17.8 | 34.3 |
| 5 | 1150 | 100 | 5.1 | 1 | 22.1 | 13.9 | 43.1 |
| 6 | 1175 | 100 | 5.1 | 2 | 30.0 | 14.0 | 42.7 |
| 7 | 1200 | 100 | 5.1 | 3 | 49.6 | 12.3 | 35.8 |

From these experiments, increasing $H_2$:$CH_4$ molar ratio resulted in an increase in the content of $C_2$ hydrocarbons in the product and an overall increase in selectivity to $C_2^+$ hydrocarbons.

EXAMPLES 8-11

Examples 8-11 were performed as described with respect to Example 3. However, different methane conversion conditions of temperature (Temp.), absolute pressure (Pressure), residence time (Tres), and $H_2$:$CH_4$ molar ratio ($H_2$:$CH_4$) were tested, as summarized in the table below, which also provides the performance parameters of $C_2$ hydrocarbon content (Prod. $C_2$) and benzene and higher hydrocarbon content (Prod. $C_6^+$), as determined in the product, in addition to methane conversion ($XCH_4$).

Summary Table, Examples 8-11

| Example | Temp., ° C. | Pressure, kPa | TRes, sec | $H_2$:$CH_4$, molar | Prod. $C_2$, vol-% | Prod. $C_6^+$, vol-% | $XCH_4$, wt-% |
|---|---|---|---|---|---|---|---|
| 8 | 1075 | 100 | 2.0 | 0.5 | 87.9 | 4.3 | 3.4 |
| 9 | 1075 | 200 | 2.8 | 0.5 | 76.8 | 11.4 | 6.9 |
| 10 | 1175 | 300 | 3.0 | 0.5 | 41.7 | 24.6 | 19.2 |
| 11 | 1200 | 450 | 2.8 | 0.5 | 21.4 | 22.9 | 24.5 |

Figure 7:
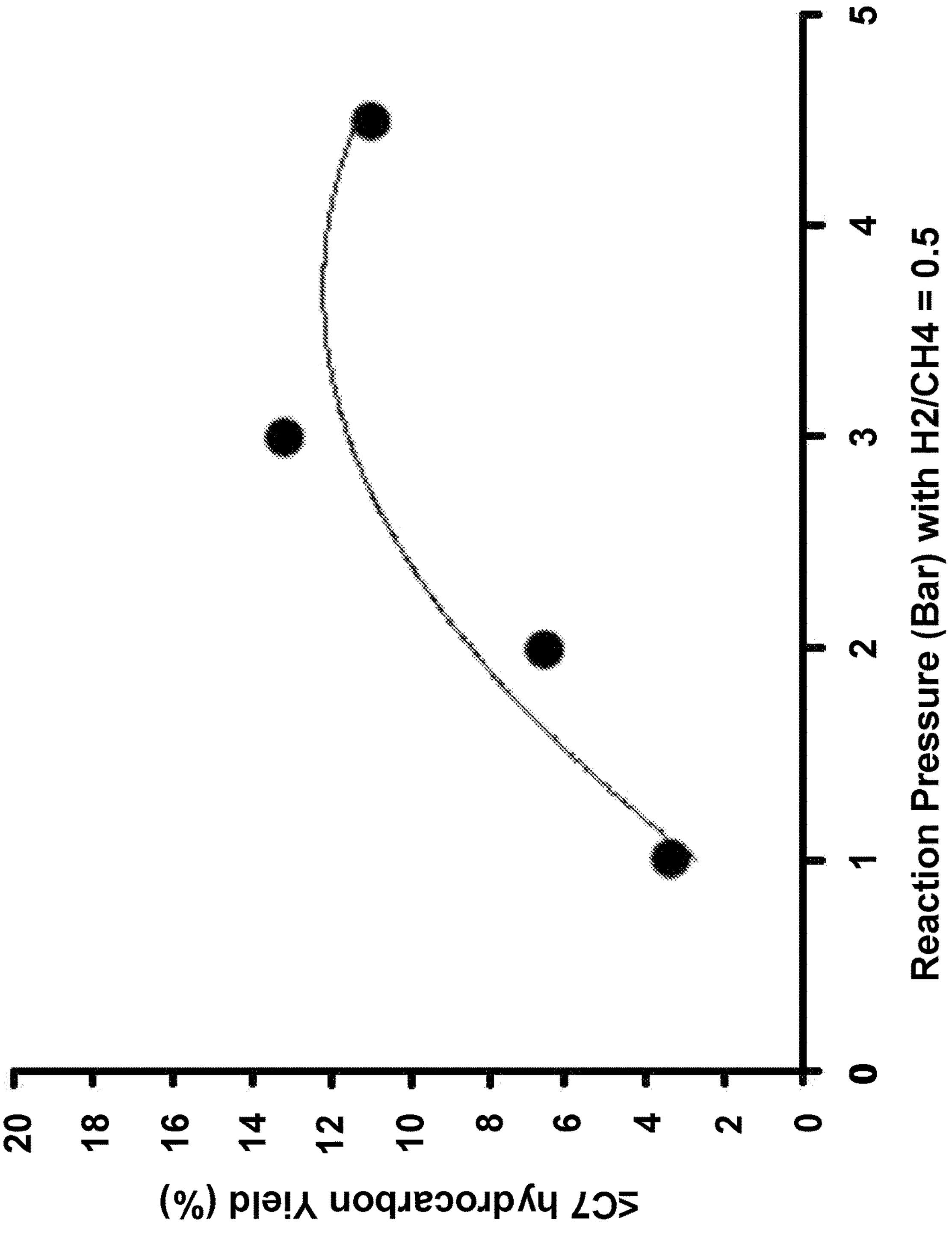
FIG. 7 depicts the product composition, in terms of $C_2$-$C_7$ hydrocarbons, as a function of reaction pressure.

From these experiments, at a temperature of 1075° C., increasing pressure in the methane conversion reactor resulted in a decrease in the content of $C_2$ hydrocarbons in the product and also a decrease in selectivity to these hydrocarbons. However, the content of $C_6^+$ hydrocarbons in the product, as well as the selectivity to these hydrocarbons, increased, as well as the methane conversion. Consequently, with respect to the particular temperature and $H_2$:$CH_4$ molar ratio used in this set of examples, the total hydrocarbon yield increased up to a pressure of about 3 atmospheres (0.3 MPa). The product composition, in terms of the content of $C_2$-$C_7$ hydrocarbons, as a function of reaction pressure, is shown in FIG. 7.

Overall, aspects of the invention are directed to processes and systems for converting methane in a methane-containing feed to higher hydrocarbons, which may be considered higher value components relative to methane, in view of various possible uses industrially. Such processes and systems may advantageously exhibit improved process economics compared to known processes, by virtue of achieving improvements in one or more performance parameters (e.g., methane conversion and selectivities to desired $C_2^+$ hydrocarbons) as described above. Those having skill in the art, with the knowledge gained from the present disclosure, will recognize that various changes can be made to these processes in attaining these and other advantages, without departing from the scope of the present disclosure. As such, it should be understood that the features of the disclosure are susceptible to modification, alteration, changes, or substitution without departing from the scope of this disclosure. The specific embodiments described herein are for illustrative purposes only, and not limiting of the invention as set forth in the appended claims.

The invention claimed is:

1. A process for converting methane in a methane-containing feed to $C_2^+$ hydrocarbons, the process comprising providing the methane-containing feed to a methane conversion reactor, increasing a hydrogen concentration or hydrogen partial pressure in the methane conversion reactor, and operating under non-oxidizing methane conversion conditions to obtain a product comprising the $C_2^+$ hydrocarbons, wherein the non-oxidizing methane conversion conditions include an absolute pressure of less than about 1 megapascal (MPa) and a residence time of less than about 60 seconds.

2. The process of claim 1, wherein the methane conversion conditions further include a temperature from about 750° C. to about 2000° C. and a hydrogen content in the methane conversion reactor of at least about 10 vol-%.

3. The process of claim 1, wherein the methane-containing feed comprises at least about 20 vol-% of methane.

4. The process of claim 1, wherein the methane-containing feed comprises at least about 90 vol-% of hydrogen and methane in combination.

5. The process of claim 1, wherein the methane-containing feed comprises less than about 5 vol-% of a combined amount of $H_2O$, $CO_2$, $O_2$, and $H_2S$.

6. The process of claim 1, wherein the $C_2^+$ hydrocarbons include one or more $C_2$ hydrocarbons and one or more aromatic hydrocarbons.

7. The process of claim 6, wherein the one or more $C_2$ hydrocarbons include ethane, ethylene, and acetylene.

8. The process of claim 6, wherein the one or more aromatic hydrocarbons include benzene, one or more $C_1$- or $C_2$-substituted benzenes, and one or more fused ring aromatic hydrocarbons.

9. The process of claim 1, wherein a conversion of methane in the methane-containing feed is at least about 15 wt-%.

10. The process of claim 1, wherein methane in the methane-containing feed is converted with a selectivity to the $C_2^+$ hydrocarbons of at least about 85 wt-%.

11. The process of claim 1, wherein methane in the methane-containing feed is converted with a selectivity to $C_2$ hydrocarbons of at least about 35 wt-%.

12. The process of claim 1, wherein methane in the methane-containing feed is converted with a selectivity to single ring aromatic hydrocarbons of at least about 45 wt-%.

13. The process of claim 1, wherein methane in the methane-containing feed is converted with a selectivity to coke of less than about 3 wt-%.

14. The process of claim 1, wherein the methane conversion reactor contains a catalyst comprising a methane conversion active metal, or a compound of a methane conversion active metal, wherein the methane conversion active metal is selected from the group consisting of Fe, Cr, Mn, V, Mo, and W.

15. The process for converting methane of claim 1, further comprising separating the product comprising the $C_2^+$ hydrocarbons by condensing from the product a liquid, said liquid being enriched in the one or more aromatic hydrocarbons.

16. The process of claim 15, wherein the separating provides a vapor, said vapor being enriched in hydrogen and unconverted methane.

17. The process of claim 16, wherein the vapor is further enriched in the one or more $C_2$ hydrocarbons.

18. The process of claim 16, further comprising recycling at least a portion of the vapor to the methane conversion reactor.

* * * * *